United States Patent
Yuan et al.

(10) Patent No.: US 6,511,987 B1
(45) Date of Patent: Jan. 28, 2003

(54) BICYCLIC AND TRICYCLIC HETEROAROMATIC COMPOUNDS

(75) Inventors: Jun Yuan, Guilford, CT (US); Pamela Albaugh, Carmel, IN (US); Kenneth Shaw, Weston, CT (US); Alan Hutchinson, Madison, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/709,887

(22) Filed: Nov. 10, 2000

Related U.S. Application Data

(60) Provisional application No. 60/165,054, filed on Nov. 12, 1999.

(51) Int. Cl.[7] .................. C07D 471/04; A61K 31/437; A61P 25/24
(52) U.S. Cl. ........................ 514/292; 546/85; 546/86; 546/87; 544/333; 544/405; 514/255.05; 514/256
(58) Field of Search .............. 546/85, 87, 86; 514/292, 255.05, 256; 544/333, 405

(56) References Cited

U.S. PATENT DOCUMENTS 5,955,465 A 9/1999 Chen et al. .................. 514/267

FOREIGN PATENT DOCUMENTS

| WO | 9602509 | 2/1996 |
|---|---|---|
| WO | 99/06407 | 2/1999 |
| WO | 99/36423 | 7/1999 |
| WO | 99/50385 | 10/1999 |
| WO | 00/12505 | 3/2000 |
| WO | 00/58303 | 10/2000 |
| WO | 01/34603 | 5/2001 |

*Primary Examiner*—Mukund J. Shah
*Assistant Examiner*—Kahsay Habte
(74) *Attorney, Agent, or Firm*—McDonnell Boehnen Hulbert & Berghoff

(57) ABSTRACT

Disclosed are compounds of the formula:

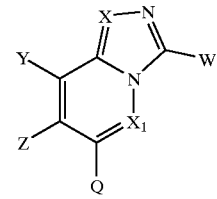

and the pharmaceutically acceptable salts thereof, wherein W, Q, X, $X_1$, Y and Z are as defined herein. These compounds bind with high selectivity and/or high affinity to the benzodiazepine site of $GABA_A$ receptors and are therefore useful in the treatment of central nervous system (CNS) diseases and as probes for the localization of $GABA_A$ receptors in tissue samples. Also disclosed are intermediates useful in the preparation of these compounds.

59 Claims, No Drawings

BICYCLIC AND TRICYCLIC HETEROAROMATIC COMPOUNDS

This application claims the benefit of Provisional application Ser. No. 60/165,054, filed Nov. 12, 1999.

FIELD OF THE INVENTION

This invention relates to heterocyclic derivatives that bind to the benzodiazepine site of $GABA_A$ receptors. This invention also relates to pharmaceutical compositions comprising such compounds and to the use of such compounds in the treatment of central nervous system (CNS) diseases. This invention also relates to the use of these heterocyclic compounds in combination with one or more other CNS agents to potentiate the effects of the other CNS agents. Additionally this invention relates to the use such compounds as probes for the localization of $GABA_A$ receptors in tissue sections.

BACKGROUND

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least $6\alpha$, $3\beta$, $3\gamma$, $1\epsilon$, $1\delta$ and $2\pi$ subunits have been identified. It is generally accepted that native $GABA_A$ receptors are typically composed of $2\alpha$, $2\beta$, and $1\gamma$ subunits (Pritchett & Seeburg Science 1989; 245:1389–1392 and Knight et. al., Recept. Channels 1998; 6:1–18). Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et. al. Neuroch. Res. 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th\ ed.}$, 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of other CNS active compounds. For example, there is evidence that selective serotonin reuptake inhibitors (SSRIs) may show greater antidepressant activity when used in combination with $GABA_A$ selective ligands than when used alone.

SUMMARY OF THE INVENTION

This invention provides heterocyclic derivatives, particularly imidazoquinoline and 1,2,4-triazoloquinoline derivatives, that bind to the benzodiazepine site of the $GABA_A$ receptor, including human $GABA_A$ receptors. Preferably, these compounds also bind with high affinity to such receptors. More preferably, these compounds bind with high selectivity to such receptors.

The invention provides compounds of Formula I (shown below), and pharmaceutical compositions comprising compounds of Formula 1.

The invention further provides methods of treating patients suffering from CNS disorders with a therapeutically effective amount of a compound of the invention. The patient may be a human or other mammal. Treatment of humans, domesticated companion animals (pets) and livestock animals suffering from CNS disorders with a therapeutically effective amount of a compound of the invention is contemplated by the invention.

In a separate aspect, the invention provides a method of potentiating the actions of other CNS active compounds. This method comprises administering a therapeutically effective amount of a compound of the invention with another CNS active compound.

Additionally this invention provides for the use of the compounds of the invention as probes for the localization of $GABA_A$ receptors in tissue samples, in particular, tissue sections.

The invention also provides intermediate compounds that are useful in the preparation of compounds of Formula 1.

A broad aspect of the invention is directed to compounds of Formula 1:

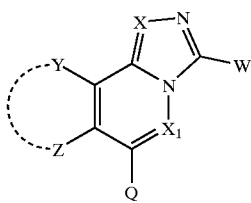

Formula I

And the pharmaceutically acceptable salts thereof, wherein:
X represents N or $CR_1$, wherein
$R_1$ is hydrogen, halogen, hydroxy, cyano, nitro, amino, $C_1$–$C_6$ alkyl, $C_1$–$C_6$ alkoxy, trifluoromethyl, trifluoromethoxy, mono or di($C_1$–$C_6$)alkylamino, or amino($C_1$–$C_6$)alkyl;

$X_1$ represents N, CH, or $C_1$–$C_6$alkyl;

Y and Z are independently hydrogen, halogen, hydroxy, cyano, nitro, amino, $C_1$–$C_6$ alkyl, $C_1$–$C_6$alkoxy, trifluoromethyl, trifluoromethoxy, mono or di($C_1$–$C_6$) alkylamino, or amino($C_1$–$C_6$)alkyl; or Y and Z together form an arylene ring or a $C_3$–$C_8$ cycloalkylene ring, each of which is optionally substituted with up to four groups $R_2$ independently chosen at each occurrence from halogen, hydroxy, cyano, nitro, amino, $C_1$–$C_6$ alkyl, $C_1$–$C_6$alkoxy, trifluoromethyl, trifluoromethoxy, mono or di($C_1$–$C_6$)alkylamino, and amino($C_1$–$C_6$) alkyl;

W is aryl or heteroaryl, each of which is optionally substituted with one or more groups $R_A$, wherein each $R_A$ is independently
  i) halogen, hydroxy, cyano, nitro, amino, $C_1$–$C_6$alkoxy, trifluoromethyl, trifluoromethoxy, —$SO_2NH_2$, —$SO_2NH(C_1$–$C_8$ alkyl), —$SO_2N(C_{1-8}$ alkyl)($C_1$–$C_8$ alkyl), —NH($C_1$–$C_8$ alkyl), —N($C_1$–$C_8$ alkyl) ($C_{1-8}$ alkyl), —N($C_1$–$C_8$ alkyl)CO($C_1$–$C_8$ alkyl), —N($C_1$–$C_8$ alkyl)$CO_2$($C_1$–$C_8$ alkyl), —$CONH_2$, —CONH($C_1$–$C_8$ alkyl), —CON($C_1$–$C_8$ alkyl) ($C_1$–$C_8$ alkyl), —$CO_2$($C_1$–$C_8$ alkyl), —S($C_1$–$C_8$ alkyl), —SO($C_1$–$C_8$ alkyl), or —$SO_2$($C_1$–$C_8$ alkyl);
  ii) aryl or heteroaryl, each of which is optionally substituted with one or two groups independently selected from halogen, hydroxy, cyano, nitro, amino, $C_1$–$C_6$ alkyl, $C_1$–$C_6$alkoxy, trifluoromethyl, trifluoromethoxy, mono or di($C_1$–$C_6$)alkylamino, and amino ($C_1$–$C_6$) alkyl;
  iii) $C_1$–$C_8$alkyl, $C_2$–$C_8$alkenyl, $C_2$–$C_8$ alkynyl, $C_3$–$C_8$cycloalkyl, $C_3$–$C_8$cycloalkyl ($C_1$–$C_3$ alkyl), $C_3$–$C_8$cycloalkenyl, each of which is unsubstituted or substituted by one or more substituents independently selected from hydroxy, oxo, halogen, $C_1$–$C_6$alkoxy, —$CONH_2$, —CONH$C_1$–$C_6$alkyl, —CON($C_1$–$C_6$alkyl) ($C_1$–$C_6$alkyl), —COOH, and —$CO_2C_1$–$C_6$alkyl; or
  iv) $NR_4R_5$, wherein $R_4$, $R_5$ and the nitrogen to which they are attached form a monocyclic or bicyclic ring optionally containing one or more of oxo, O, S, SO, $SO_2$, or $NR_6$ wherein $R_6$ is hydrogen, $C_1$–$C_6$alkyl, or Ar—($C_1$–$C_6$alkyl) where
    Ar is aryl or heteroaryl, each of which is optionally substituted by one or two groups independently selected from halogen, hydroxy, cyano, nitro, amino, $C_1$–$C_6$ alkyl, $C_1$–$C_6$alkoxy, trifluoromethyl, trifluoromethoxy, mono or di($C_1$–$C_6$)alkylamino, and amino($C_1$–$C_6$)alkyl; and Q is selected Formulas III, IV and V:

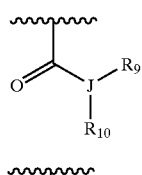

Formula III

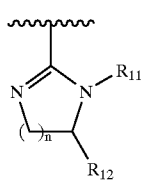

Formula IV

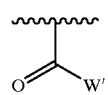

Formula V wherein:

J is N or $C_1$–$C_8$ alkylene; and $R_9$ and $R_{10}$ are independently hydrogen, $C_1$–$C_8$ alkyl, or $Ar_1$, wherein $Ar_1$ is aryl or heteroaryl, each of which may be substituted with one or two of $R_B$, where each $R_B$ independently carries the definition of $R_A$; or $R_9$, $R_{10}$ and the atom to which they are attached form a 4-to 8-membered monocyclic or bicyclic ring optionally containing one or more double bonds or one or more of oxo, O, S, SO, $SO_2$, or N—$R_8$ wherein $R_8$ is hydrogen, $C_1$–$C_8$ alkyl, or $Ar_1$—($C_1$–$C_8$ alkyl); wherein $Ar_1$ is optionally substituted with one or two of $R_B$, where each $R_B$ independently carries the definition of $R_A$; and wherein the monocyclic or bicyclic ring is optionally substituted with $C_1$–$C_6$ alkyl or hydroxy($C_1$–$C_6$) alkyl;

$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$) alkanoyl; and $R_{12}$ is selected from the group consisting of hydrogen, $C_1$–$C_8$ alkyl, and $C_1$–$C_8$ alkoxy; or $R_{11}$ and $R_{12}$ together with the atoms to which they are attached form a 5–8 membered monocyclic ring which is optionally substituted with one or more of halogen, hydroxy, cyano, nitro, amino, $C_1$–$C_6$ alkyl, $C_1$–$C_6$alkoxy, trifluoromethyl, trifluoromethoxy, mono or di($C_1$–$C_6$)alkylamino, or amino($C_1$–$C_6$) alkyl; and n is 1, 2, 3, or 4; and W'
  (i) independently carries the same definition as W;
  (ii) represents —OR where R is $C_1$–$C_8$ alkyl or aryl($C_1$–$C_6$)alkyl; or
  (iii) is $M_5$ where $M_5$ is hydroxy, $C_1$–$C_8$ alkyl, aryl ($C_1$–$C_6$)alkyl or —N(($C_1$–$C_4$ alkyl) ($C_1$–$C_4$ alkoxy).

DETAILED DESCRIPTION OF THE INVENTION

For compounds of Formula I (above) preferred aryl and heteroaryl groups representing the variable W include, but are not limited to the groups $W_1$ defined as follows: $W_1$: phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl or benzopyrazolyl, each of which is optionally substituted by one or more groups independently chosen at each occurrence from
  halogen, hydroxy, cyano, nitro, amino, $C_1$–$C_6$alkoxy, trifluoromethyl, trifluoromethoxy, —$SO_2NH_2$, —$SO_2NH(C_1$–$C_8$ alkyl), —$SO_2N(C_{1-8}$ alkyl) ($C_1$–$C_8$ alkyl), —NH($C_1$–$C_8$ alkyl), —N($C_1$–$C_8$ alkyl) ($C_{1-8}$ alkyl), —N($C_1$–$C_8$ alkyl)CO($C_1$–$C_8$ alkyl), —N($C_1$–$C_8$ alkyl)$CO_2$($C_1$–$C_8$ alkyl), —$CONH_2$, —CONH($C_1$–$C_8$ alkyl), —CON($C_1$–$C_8$ alkyl) ($C_1$–$C_8$ alkyl), —$CO_2$ ($C_1$–$C_8$ alkyl), —S($C_1$–$C_8$ alkyl), —SO($C_1$–$C_8$ alkyl), —$SO_2$($C_1$–$C_8$ alkyl), and phenyl.

Especially preferred groups representing the variable W includes the groups $W_2$, wherein $W_2$ represents phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl or benzopyrazolyl, each of which is optionally substituted by one or more groups independently chosen at each occurrence from halogen, hydroxy, cyano, nitro, amino, $C_1$–$C_6$alkoxy, trifluoromethyl, trifluoromethoxy, —$SO_2NH_2$, —$SO_2NH(C_1$–$C_8$ alkyl), —$SO_2N(C_{1-8}$ alkyl) ($C_1$–$C_8$ alkyl), —$NH(C_1$–$C_8$ alkyl), —$N(C_1$–$C_8$ alkyl) ($C_{1-8}$ alkyl), —$N(C_1$–$C_8$ alkyl)CO($C_1$–$C_8$ alkyl), —$N(C_1$–$C_8$ alkyl)$CO_2$($C_1$–$C_8$ alkyl), —$CONH_2$, —$CONH(C_1$–$C_8$ alkyl), —$CON(C_1$–$C_8$ alkyl) ($C_1$–$C_8$ alkyl), —$CO_2$ ($C_1$–$C_8$ alkyl), —$S(C_1$–$C_8$ alkyl), —$SO(C_1$–$C_8$ alkyl), —$SO_2(C_1$–$C_8$ alkyl), and phenyl.

A preferred arylene ring formed by Y and Z is benzo. Particularly preferred benzo rings are unsubstituted or substituted with one, two, or three, more preferably one or two, of $R_2$ where each $R_2$ is the same as or different than every other $R_2$. Preferred benzo substituents are halogen, hydroxy, $C_1$–$C_6$ alkyl, $C_1$–$C_6$ alkoxy, —$NO_2$, —CN, amino, —NH($C_1$–$C_6$ alkyl), and —N($C_1$–$C_6$ alkyl)$_2$. Highly preferred benzo substituents are halogen, hydroxy, $C_1$–$C_6$ alkyl, $C_1$–$C_6$ alkoxy, amino, —NH($C_1$–$C_6$ alkyl), and —N($C_1$–$C_6$ alkyl)$_2$.

Preferred cycloalkylene rings formed by Y and Z are 5-, 6-, and 7-membered cycloalkylene rings. Particularly preferred are 5-, 6-, and 7-membered cycloalkylene rings are that are unsubstituted or are substituted with one, two, or three, preferably one or two, of $R_2$ where each $R_2$ is the same as or different than every other $R_2$. Preferred cycloalkylene substituents are halogen, hydroxy, $C_1$–$C_6$ alkyl, $C_1$–$C_6$ alkoxy, —$NO_2$, —CN, —$SO_2NH_2$, amino, —NH($C_1$–$C_6$ alkyl), and —N($C_1$–$C_6$ alkyl)$_2$. Highly preferred cycloalkylene substituents are halogen, hydroxy, $C_1$–$C_6$ alkyl, $C_1$–$C_6$ alkoxy, amino, —NH($C_1$–$C_6$ alkyl), and —N($C_1$–$C_6$ alkyl)$_2$.

A preferred group of compounds of the invention includes those represented by Formula A-3

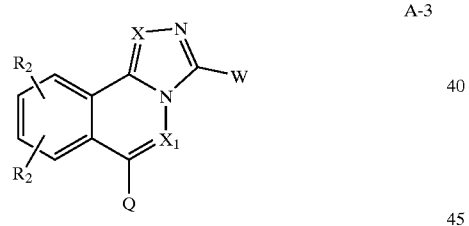

A-3 wherein $R_2$, Q, $X_1$, X and W are as defined for Formula I and $R_2$ is independently chosen at each occurrence.

Preferred compounds of Formula A-3 include compounds where

W is phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl or benzopyrazolyl, each of which is unsubstituted or substituted with one or more substituents independently selected from the group consisting of: halogen, hydroxy, cyano, nitro, amino, $C_1$–$C_8$alkyl, $C_1$–$C_6$alkoxy, trifluoromethyl, trifluoromethoxy, —$SO_2NH_2$, —$SO_2NH(C_1$–$C_8$ alkyl), —$SO_2N(C_{1-8}$ alkyl) ($C_1$–$C_8$ alkyl), —$NH(C_1$–$C_8$ alkyl), —$N(C_1$–$C_8$ alkyl) ($C_{1-8}$ alkyl), —$N(C_1$–$C_8$ alkyl)CO($C_1$–$C_8$ alkyl), —$N(C_1$–$C_8$ alkyl)$CO_2$($C_1$–$C_8$ alkyl), —$CONH_2$, —$CONH(C_1$–$C_8$ alkyl), —$CON(C_1$–$C_8$ alkyl) ($C_1$–$C_8$ alkyl), —$CO_2$($C_1$–$C_8$ alkyl), —$S(C_1$–$C_8$ alkyl), —$SO(C_1$–$C_8$ alkyl), —$SO_2$($C_1$–$C_8$ alkyl) and phenyl.

Even more preferred compounds of Formula A-3 include those where $R_2$ is independently chosen at each occurrence from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V:

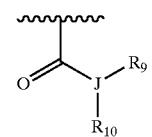

Formula III

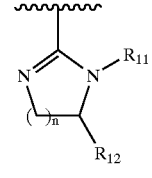

Formula IV

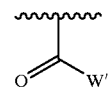

Formula V wherein:

J is N or $C_1$–$C_8$ alkylene; and $R_9$ and $R_{10}$ are independently hydrogen, $C_1$–$C_8$ alkyl; or $R_9$, $R_{10}$ and the atom to which they are attached form a 4-to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy ($C_1$–$C_6$) alkyl;

$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$) alkanoyl; and $R_{12}$ is selected from the group consisting of hydrogen, $C_1$–$C_8$ alkyl, and $C_1$–$C_8$ alkoxy; or $R_{11}$ and $R_{12}$ together with the atoms to which they are attached form a 5–8 membered monocyclic ring, which is optionally substituted with $C_1$–$C_6$ alkyl; and n is 1, 2, 3, or 4;

W' phenyl, pyridyl, or naphthyl; and

W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

Other preferred compounds of Formula A-3 include compounds where $X_1$ is $CR_1$ and $R_1$ is hydrogen or $C_1$–$C_6$alkyl.

Preferred compounds of Formula A-3 also include compounds wherein $X_1$ is $CR_1$ and $R_1$ is hydrogen or $C_1$–$C_6$alkyl, and W has the definition of $W_1$ or more preferably W has the definition of $W_2$.

Also preferred are compounds of Formula A-3 wherein $X_1$ is $CR_1$ and $R_1$ is hydrogen or $C_1$–$C_6$alkyl;

$R_2$ is independently selected at each occurrence from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V wherein:

J is N or $C_1$–$C_8$ alkylene; and $R_9$ and $R_{10}$ are independently hydrogen, $C_1$–$C_8$ alkyl; or $R_9$ $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_6$)alkyl;

$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and $R_{12}$ is selected from the group consisting of hydrogen, $C_1$–$C_8$ alkyl, and $C_1$–$C_8$ alkoxy; or $R_{11}$ and $R_{12}$ together with the atoms to which they are attached form a 5–8 membered monocyclic ring, which is optionally substituted with $C_1$–$C_6$ alkyl; and n is 1, 2, 3, or 4;

W' phenyl, pyridyl, or naphthyl; and

W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

Preferred W groups of Formula A-3 are those carrying k-2 substituents where k is the number of hydrogen atoms on the aryl or heteroaryl group defined by W. More preferably, the W groups carry k-3 substituents. The most preferred W groups are those carrying 1 or 2 substituents, and those substituents are most preferably hydroxy, halogen, $C_1$–$C_6$ alkyl, $C_1$–$C_6$ alkoxy, trifluoromethyl, trifluoromethoxy, amino or mono- or di($C_1$–$C_6$) alkylamino.

Another preferred group of compounds of the invention are those depicted by Formula A-6

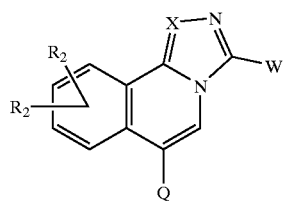

A-6 wherein $R_2$, Q, and X are defined as in Formula I, $R_2$ is independently defined at each occurrence, and W is $W_1$.

More preferred are compounds of Formula A-6 are those where $R_2$, Q, and X are defined as in Formula I, and W is $W_2$.

More preferred are compounds of Formula A-6 include those where $R_2$ are independently selected at each occurrence from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V:

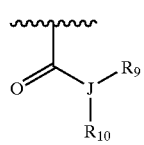

Formula III

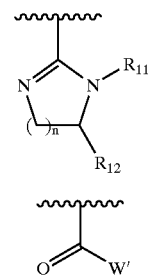

Formula IV

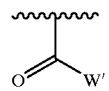

Formula V wherein:

J is N or $C_1$–$C_8$ alkylene; and $R_9$ and $R_{10}$ are independently hydrogen, $C_1$–$C_8$ alkyl; or $R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_6$)alkyl;

$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and $R_{12}$ is selected from the group consisting of hydrogen, $C_1$–$C_8$ alkyl, and $C_1$–$C_8$ alkoxy; or $R_{11}$ and $R_{12}$ together with the atoms to which they are attached form a 5–8 membered monocyclic ring, which is optionally substituted with $C_1$–$C_6$alkyl; and n is 1, 2, 3, or 4;

W' phenyl, pyridyl, or naphthyl; and

W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

Preferred W groups of Formula A-6 are those carrying k-2 substituents where k is the number of hydrogen atoms on the aryl or heteroaryl group defined by W. More preferably, the W groups carry k-3 substituents. The most preferred W groups are those carrying 1 or 2 substituents, and those substituents are most preferably hydroxy, halogen, $C_1$–$C_6$ alkyl, $C_1$–$C_6$ alkoxy, trifluoromethyl, trifluoromethoxy, amino or mono- or di($C_1$–$C_6$)alkylamino.

Another preferred group of compounds of the invention is represented by Formula A-9, i.e., compound where both X and $X_1$ are both CH,

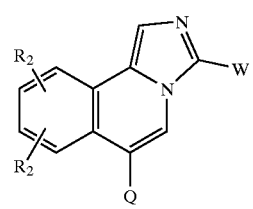

A-9 wherein $R_1$, $R_2$, and Q are as defined as in Formula 1, and W is $W_1$.

More preferred are compounds of Formula A-9 include those wherein $R_2$ and Q are as defined in Formula I, and W is $W_1$.

Most preferred compounds of formula A-9 are those wherein $R_2$ is independently selected at each occurrence from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V:

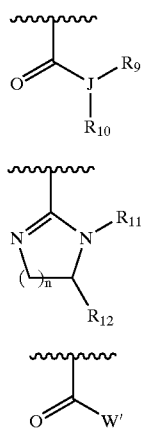

Formula III

Formula IV

Formula V

J is N or $C_1$–$C_8$ alkylene; and $R_9$ and $R_{10}$ are independently hydrogen, $C_1$–$CC_8$ alkyl; or $R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_5$) alkyl;

$R_{11}$ is selected from the group consisting of hydrogen, $C_1$–$C_8$ alkyl, $C_1$–$C_8$ alkanoyl, aryl($C_1$–$C_6$)alkyl, and aryl ($C_1$–$C_6$) alkanoyl; and $R_{12}$ is selected from the group consisting of hydrogen, $C_1$–$C_8$ alkyl, and $C_1$–$C_8$ alkoxy; or $R_{11}$ and $R_{12}$ together with the atoms to which they are attached form a 5–8 membered monocyclic ring, which is optionally substituted with $C_1$–$C_6$alkyl; and n is 1, 2, 3, or 4;

W' phenyl, pyridyl, or naphthyl; and

W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

Preferred W groups of Formula A-9 are those carrying k-2 substituents where k is the number of hydrogen atoms on the aryl or heteroaryl group defined by W. More preferably, the W groups carry k-3 substituents. The most preferred W groups are those carrying 1 or 2 substituents, and those substituents are most preferably hydroxy, halogen, $C_1$–$C_6$ alkyl, $C_1$–$C_6$ alkoxy, trifluoromethyl, trifluoromethoxy, amino or mono- or di($C_1$–$C_6$)alkylamino.

Still another preferred group of compounds is represented by Formula A-12.

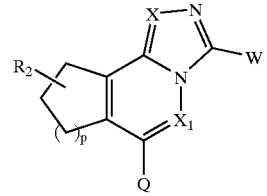

A-12 wherein
wherein $R_1$, Q, and X are as defined in Formula I and p is 1, 2, 3, and 4; and W is $W_1$.

More preferred compounds of Formula A-12 are those where $R_2$, Q, and X are as defined in Formula 1;
p is 1, 2, 3, or 4; and
W is $W_2$.

Even more preferred compounds of Formula 12 are those wherein $R_2$ is selected from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V:

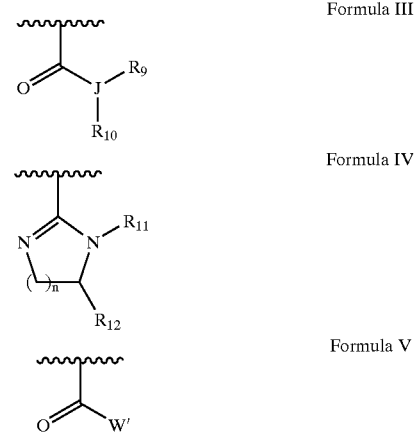

Formula III

Formula IV

Formula V wherein:
J is N or $C_1$–$C_8$ alkylene; and
$R_9$ and $R_{10}$ are independently hydrogen, $C_1$–$C_8$ alkyl; or $R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_6$)alkyl;

$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and $R_{12}$ is selected from the group consisting of hydrogen, $C_1$–$C_8$ alkyl, and $C_1$–$C_8$ alkoxy; or $R_{11}$ and $R_{12}$ together with the atoms to which they are attached form a 5–8 membered monocyclic ring, which is optionally substituted with $C_1$–$C_6$ alkyl; and n is 1, 2, 3, or 4;
W' phenyl, pyridyl, or naphthyl; and
W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

Preferred compounds of the invention are also encompassed by Formula A-15

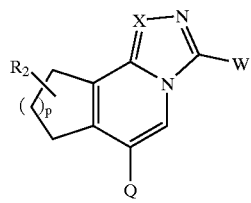

A-15 wherein $R_1$, Q, and X are as defined in Formula 1; p is 1, 2, 3, or 4; and W is $W_1$.

More compounds of Formula A-15 are those wherein
$R_2$, Q, and X are as defined in Formula 1;
p is 1, 2, or 3; and
W is $W_2$.

Even more preferred compounds of Formula A-15 are those where
$R_2$ is independently selected at each occurrence from the group consisting of $C_1$–$C_6$ alkyl, $C_1$–$C_6$ alkoxy, halogen, hydroxy, trifluoromethyl and trifluoromethoxy;
Q is selected from the group consisting of Formulas III, IV and V:

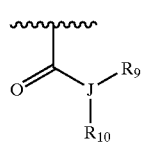

Formula III

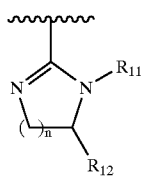

Formula IV

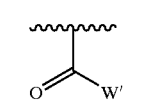

Formula V wherein:
J is N or $C_1$–$C_8$ alkylene; and
$R_9$ and $R_{10}$ are independently hydrogen, $C_1$–$C_8$ alkyl; or
$R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_6$)alkyl;
$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and $R_{12}$ is selected from the group consisting of hydrogen, $C_1$–$C_8$ alkyl, and $C_1$–$C_8$ alkoxy; or
$R_{11}$ and $R_{12}$ together with the atoms to which they are attached form a 5–8 membered monocyclic ring, which is optionally substituted with $C_1$–$C_6$ alkyl; and
n is 1, 2, 3, or 4;
W' phenyl, pyridyl, or naphthyl; and
W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

Preferred compounds of the invention are also encompassed by Formula A-17, i.e., compounds where Y and Z are not joined to form an aryl ring.

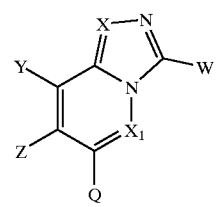

A-17 wherein X, $X_1$, and Q are defined as in Formula I, and W is $W_1$; and
Y and Z are independently selected from hydrogen, halogen, hydroxy, cyano, nitro, amino, $C_1$–$C_6$ alkyl, $C_1$–$C_6$alkoxy, trifluoromethyl, trifluoromethoxy, mono or di($C_1$–$C_6$)alkylamino, amino($C_1$–$C_6$)alkyl.

More preferred compounds of Formula A-17 are those wherein X, $X_1$, and Q are defined as in Formula I, and W is $W_2$; and Y and Z are independently selected from hydrogen, halogen, hydroxy, cyano, nitro, amino, $C_1$–$C_6$ alkyl, $C_1$–$C_6$alkoxy, trifluoromethyl, trifluoromethoxy, mono or di($C_1$–$C_6$)alkylamino, amino($C_1$–$C_6$)alkyl.

Even more preferred are compounds of Formula A-17 wherein
X is N or CH; and
Q is selected from the group consisting of Formulas III, IV and V:

Formula III

Formula IV

Formula V wherein:
J is N or $C_1$–$C_8$ alkylene; and
$R_9$ and $R_{10}$ are independently hydrogen, $C_1$–$C_8$ alkyl; or R$_9$, R$_{10}$ and the atom to which they are attached form a 4- to 8-membered monocyclic or bicyclic ring, which may contain one or more double bonds or one or more of oxo, O, S, SO, SO$_2$, or N—R$_8$ wherein R$_8$ is hydrogen, C$_1$–C$_8$ alkyl; wherein the monocyclic or bicyclic ring is optionally substituted with C$_1$–C$_6$ alkyl or hydroxy(C$_1$–C$_6$)alkyl;

R$_{11}$ is selected from the group consisting of hydrogen, C$_1$–C$_8$ alkyl, C$_1$–C$_8$ alkanoyl, aryl(C$_1$–C$_6$)alkyl, and aryl(C$_1$–C$_6$)alkanoyl; and R$_{12}$ is selected from the group consisting of hydrogen, C$_1$–C$_8$ alkyl, and C$_1$–C$_8$ alkoxy; or R$_{11}$ and R$_{12}$ together with the atoms to which they are attached form a 5–8 membered monocyclic ring, which is optionally substituted with C$_1$–C$_6$ alkyl; and n is 1, 2, 3, or 4;

W' phenyl, pyridyl, or naphthyl; and

W is phenyl, thienyl, isoxazolyl, or pyridyl, each of which is unsubstituted or substituted with one or more substituents independently selected from the group consisting of halogen, C$_1$–C$_6$ alkyl, C$_1$–C$_6$ alkoxy, trifluoromethyl, trifluoromethoxy, and hydroxy.

Other preferred compounds are represented by Formula A-18

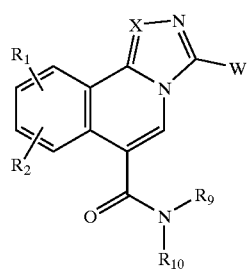

A-18

W is phenyl, isoxazolyl, thienyl, pyridyl, quinolyl, each of which is optionally substituted with one, two, or three of V$_1$, V$_2$ and V$_3$, where V$_1$, V$_2$, and V$_3$ independently represent halogen, hydroxy, C$_1$–C$_6$ alkyl, C$_1$–C$_8$ alkoxy, —NO$_2$, —CN, amino, —NH(C$_1$–C$_8$ alkyl), or —N(C$_1$–C$_8$ alkyl) (C$_1$–C$_8$ alkyl);

R$_1$ and R$_2$ independently represent hydrogen, halogen, hydroxy, C$_1$–C$_6$ alkyl, C$_1$–C$_8$ alkoxy, —NO$_2$, —CN, amino, —NH(C$_1$–C$_8$ alkyl), or —N(C$_1$–C$_8$ alkyl) (C$_1$–C$_8$ alkyl);

X is nitrogen or CR$_{111}$, where R$_{111}$ is hydrogen, halogen, hydroxy, C$_1$–C$_6$ alkyl, C$_1$–C$_8$ alkoxy, —NO$_2$, —CN, amino, —NH(C$_1$–C$_8$ alkyl), or —N(C$_1$–C$_8$ alkyl) (C$_1$–C$_8$ alkyl); and R$_9$ and R$_{10}$ are independently hydrogen or C$_1$–C$_8$ alkyl; or NR$_9$R$_{10}$ represents a 5- to 7-membered ring optionally containing one or two double bonds, O and/or N—R$_8$ where R$_8$ is hydrogen, C$_1$–C$_8$ alkyl, or HAr—(C$_1$–C$_8$) alkyl, where HAr is phenyl, pyridinyl, or pyrimidinyl, each of which is optionally substituted with one or two halogen, hydroxy, hydroxy(C$_1$–C$_6$)alkyl, C$_1$–C$_6$ alkyl, C$_1$–C$_8$ alkoxy, —NO$_2$, —CN, amino, —NH(C$_1$–C$_8$ alkyl), or —N(C$_1$–C$_8$ alkyl) (C$_1$–C$_8$ alkyl).

More preferred compounds of Formula A-18 include those where X is nitrogen.

Still other more preferred compounds of Formula A-18 are those where X is CH or a carbon atom substituted with (C$_1$–C$_6$) alkyl.

Other preferred compounds are represented by Formula A-19

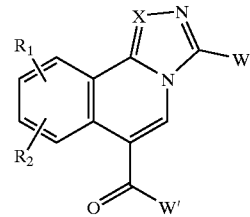

A-19

W is phenyl, isoxazolyl, thienyl, pyridyl, quinolyl, each of which is optionally substituted with one, two, or three of V$_1$, V$_2$ and V$_3$, where V$_1$, V$_2$, and V$_3$ independently represent halogen, hydroxy, C$_1$–C$_6$ alkyl, C$_1$–C$_8$ alkoxy, —NO$_2$, —CN, amino, —NH(C$_1$–C$_8$ alkyl), or —N(C$_1$–C$_8$ alkyl) (C$_1$–C$_8$ alkyl);

R$_1$ and R$_2$ independently represent hydrogen, halogen, hydroxy, C$_1$–C$_6$ alkyl, C$_1$–C$_8$ alkoxy, —NO$_2$, —CN, amino, —NH(C$_1$–C$_8$ alkyl), or —N (C$_1$–C$_8$ alkyl) (C$_1$–C$_8$ alkyl);

X is nitrogen or CR$_{111}$, where R$_{111}$ is hydrogen, halogen, hydroxy, C$_1$–C$_6$ alkyl, C$_1$–C$_8$ alkoxy, —NO$_2$, —CN, amino, —NH(C$_1$–C$_8$ alkyl), or —N(C$_1$–C$_8$ alkyl) (C$_1$–C$_8$ alkyl); and W' represents
(i) phenyl optionally substituted with one, two, or three of T$_1$, T$_2$ and T$_3$, where T$_1$, T$_2$, and T$_3$ independently represent halogen, hydroxy, C$_1$–C$_6$ alkyl, C$_1$–C$_8$ alkoxy, —NO$_2$, —CN, amino, —NH(C$_1$–C$_8$ alkyl), or —N(C$_1$–C$_8$ alkyl) (C$_1$–C$_8$ alkyl);
(ii) —OR where R is C$_1$–C$_8$ alkyl or aryl(C$_1$–C$_6$)alkyl; or
(iii) M$_5$ where M$_5$ is hydroxy, C$_1$–C$_8$ alkyl, aryl(C$_1$–C$_6$) alkyl or —N(C$_1$–C$_4$ alkyl) (C$_1$–C$_4$ alkoxy).

More preferred compounds of Formula A-19 include those where X is nitrogen.

Still other more preferred compounds of Formula A-19 are those where X is CH or a carbon atom substituted with (C$_1$–C$_6$) alkyl.

Still other preferred compounds are represented by Formula A-20

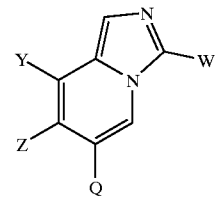

A-20 wherein and Q are as defined in Formula I, and W is W$_1$; and

Y and Z are independently selected from hydrogen, halogen, hydroxy, cyano, nitro, amino, C$_1$–C$_6$ alkyl, C$_1$–C$_6$alkoxy, trifluoromethyl, trifluoromethoxy, mono or di(C$_1$–C$_6$)alkylamino, amino(C$_1$–C$_6$)alkyl.

Especially preferred definitiona of Y and Z for Formula A-20, are hydrogen, halogen, and C$_1$–C$_6$alkyl. More preferred compounds of Formula A-20, are those where W is W$_2$.

Particularly preferred compounds of Formula A-20 are those wherein

Y and Z are independently chosen from hydrogen, halogen, and C$_1$–C$_6$alkyl, W is W$_2$; and Q is selected from the group consisting of Formulas III, IV and V:

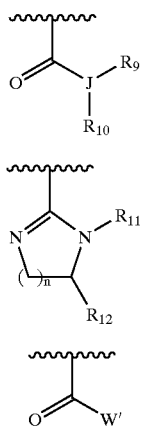

Formula III

Formula IV

Formula V wherein:
J is N or $C_1$–$C_8$ alkylene; and
$R_9$ and $R_{10}$ are independently hydrogen, $C_1$–$C_8$ alkyl; or
$R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–C, alkyl or hydroxy($C_1$–$C_6$)alkyl;
$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and
$R_{12}$ is selected from the group consisting of hydrogen, $C_1$–$C_8$ alkyl, and $C_1$–$C_6$ alkoxy; or
$R_{11}$ and $R_{12}$ together with the atoms to which they are attached form a 5–8 membered monocyclic ring, which is optionally substituted with $C_1$–$C_6$ alkyl; and
n is 1, 2, 3, or 4;
W' phenyl, pyridyl, or naphthyl; and
W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

For Formulas III, IV, and V

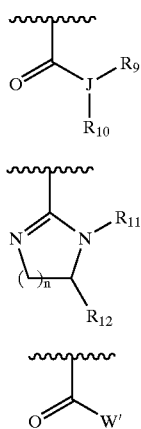

Formula III

Formula IV

Formula V

Preferred $R_8$ substituents on the hetero nitrogen (which is sometime present in the 4- to 8-membered monocyclic or bicyclic ring formed by $R_9$ and $R_{10}$) are methyl, ethyl, n-propyl and isopropyl.

Preferred $JR_9R_{10}$ groups include 1-piperidinyl optionally mono- or disubstituted with $C_1$–$C_6$ alkyl, preferably methyl or ethyl; 1-piperazinyl optionally mono- or disubstituted with $C_1$–$C_6$ alkyl, preferably methyl or ethyl; and morpholinyl optionally mono- or disubstituted with $C_1$–$C_6$ alkyl, preferably methyl or ethyl. Other preferred $JR_9R_{10}$ groups include pyrrolyl and imidazolinyl, each of which is optionally mono- or disubstituted with $C_1$–$C_3$ alkyl or hydroxy ($C_1$–$C_6$) alkyl, and preferably monosubstituted with methyl, ethyl, or hydroxymethyl.

Where the nature of the substituents permits, the groups represented by $JR_9R_{10}$ encompass various stereoisomers. While the invention encompasses racemic mixtures and mixtures of enantiomers in which one enantiomer is present in an enantiomeric excess, the preferred compounds of the invention are those where only a single, at least relatively pure, stereoisomer is present. Examples of preferred $JR_9R_{10}$ stereoisomers include the following:

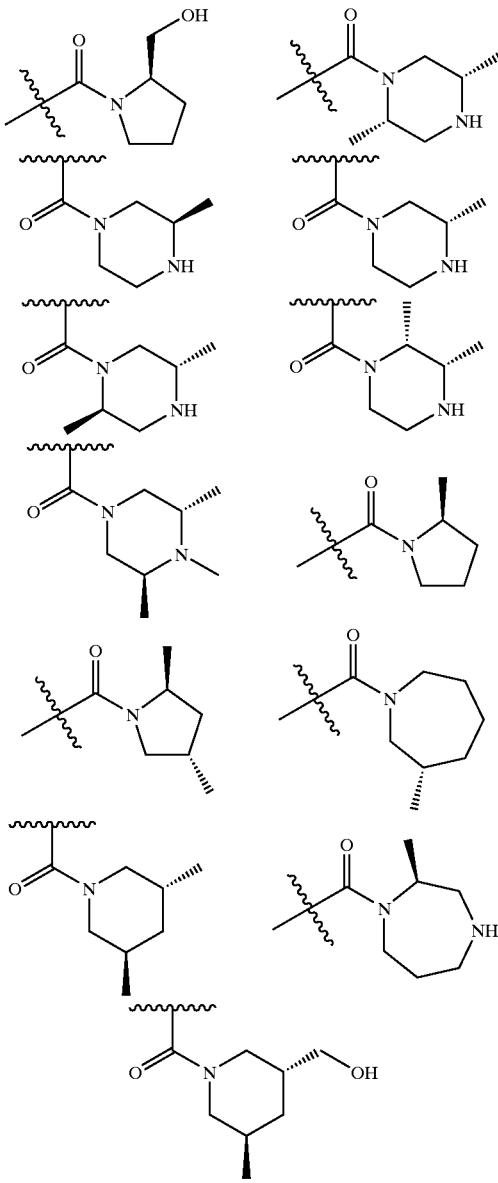

As used herein, monocyclic and bicyclic rings include both carbocyclic rings where J is, e.g., CH, and, for those rings formed by $NR_4R_5$ and $NR_4R_{10}$, nitrogen-containing carbocyclic ring systems of the type having at least one nitrogen, e.g., the nitrogen in $NR_4R_5$. Thus, in $NR_4R_5$ and $NR_9R_{10}$, the $R_4R_5$ and $R_9R_{10}$ groups together represent, for example, a $C_4$–$C_6$ straight chain alkylene group which together with the nitrogen atom to which, e.g., $R_9$ and $R_{10}$ are attached form a 5- to 7-membered ring system. This ring system may be further substituted with, e.g., $C_1$–$C_6$ alkyl or may contain one or two double bonds, O, and/or a substituted nitrogen as defined herein. In situations where J is, for example, CH, the resulting ring can contain hetero atoms such as oxygen or nitrogen giving rise to, e.g., a 4-piperidinyl group.

When J is a $C_1$–$C_8$ alkylene group, that group is attached at one terminus to the parent carbonyl and the groups $R_9$ and $R_{10}$ are attached at any position along the alkylene chain. For example, $JR_9R_{10}$ represents groups such as neopentyl, t-butyl, isopropyl, 2-ethylhexyl and n-octyl. Further, $R_9R_{10}$ may represent an alkylene group, e.g., a $C_5$ alkylene group attached to the terminus of J where is n-propyl giving rise to a cyclohexylpropyl group.

Particularly preferred compounds of Formulas A-3, A-6, and A-9, A-12, A-15, A-17, and A-20 are those where Q represents either Formula III or Formula IV. In highly preferred embodiments, Q represents Formula III where $R_9$, $R_{10}$ and the nitrogen atom to which they are attached represent mono- or di($C_1$–$C_6$)alkylamino; or $R_9$, $R_{10}$ and the nitrogen to which they are attached form a 5- or 6-membered ring.

The 5- and 6-membered rings are optionally substituted with $C_1$–$C_6$ alkyl or hydroxy($C_1$–$C_6$)alkyl, preferably hydroxymethyl, and optionally contain one hetero atom selected from oxygen, sulfur, or nitrogen. The hetero sulfur atom may be oxidized to a sulfone or sulfoxide. The hetero nitrogen is optionally substituted with $R_8$ where $R_8$ represents hydrogen or $C_1$–$C_8$ alkyl.

Other particularly preferred compounds of the invention are those where W represents optionally substituted phenyl, isoxazolyl, or thienyl. Highly preferred compounds are those where the phenyl is unsubstituted or substituted with one or two of halogen, $C_1$–$C_6$ alkyl, $C_1$–$C_6$ alkoxy, trifluoromethyl, trifluoromethoxy, or hydroxy. Other highly preferred compounds are those where W is isoxazolyl optionally substituted with $C_1$–$C_6$ alkyl, most preferably methyl, $C_1$–$C_6$ alkoxy, or halogen. The most preferred compounds are those where W is phenyl optionally substituted with one halogen, preferably chloro or fluoro, or one hydroxy. Even more preferably, the halogen or hydroxy group is in the ortho or para position of the phenyl ring.

The invention also provides intermediates of Formula A-69

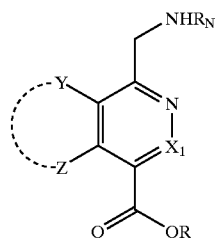

A-69 wherein Y, Z, and $X_1$ are defined as for Formula I, R is $C_1$–$C_6$alkyl, and $R_N$ is hydrogen, $C_1$–$C_6$ alkyl, or —C(O)W where W is as defined for Formula I.

Preferred intermediate compounds can be represented by Formula A-70

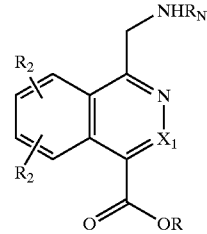

A-70 wherein $X_1$ and $R_2$ are as defined for Formula I, and R and $R_N$ are as defined in Formula A-69.

Another preferred class of intermediates is represented by Formula A-71

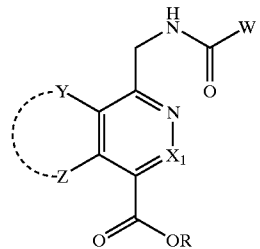

A-71 wherein $X_1$, Y, and Z are defined as in Formula I, R is $C_1$–$C_6$alkyl and

W is phenyl, pyridyl, isoxazolyl, or thienyl, each of which is unsubstituted or substituted with one or more of halogen, hydroxy, cyano, nitro, amino, $C_1$–$C_8$alkyl, $C_1$–$C_6$alkoxy, trifluoromethyl, trifluoromethoxy, —$SO_2NH_2$, —$SO_2NH(C_1$–$C_8$ alkyl), —$SO_2N(C_{1-8}$ alkyl) ($C_1$–$C_8$ alkyl), —$NH(C_1$–$C_8$ alkyl), —$N(C_1$–$C_8$ alkyl) ($C_8$ alkyl), —$N(C_1$–$C_8$ alkyl)$CO(C_1$–$C_8$ alkyl), —$N(C_1$–$C_8$ alkyl)$CO_2((C_1$–$C_8$ alkyl), —$CONH_2$, —$CONH(C_1$–$C_8$ alkyl), —$CON(C_1$–$C_8$ alkyl) ($C_1$–$C_8$ alkyl), —$CO_2(C_1$–$C_8$ alkyl), —$S(C_1$–$C_8$ alkyl), —SO ($C_1$–$C_8$ alkyl), —$SO_2(C_1$–$C_8$ alkyl) and phenyl.

More preferred are intermediate compounds of Formula A-72

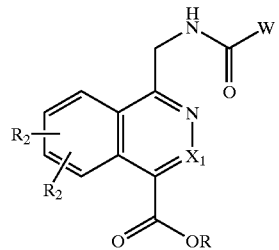

A-72 wherein $X_1$ and $R_2$ are as defined in Formula I, R is $C_1$–$C_6$alkyl, and W represents $W_2$.

Even more preferred are intermediates of Formula A-73 wherein $R_2$, is independently selected at each occurrence from the group consisting of $C_1$–$C_6$ alkyl, $C_1$–$C_6$ alkoxy, halogen, hydroxy, trifluoromethyl and trifluoromethoxy;

W is $W_2$; and $X_1$ is N or CH.

Another group of intermediate compounds useful in preparing compounds of the instant invention are those of Formula A-74

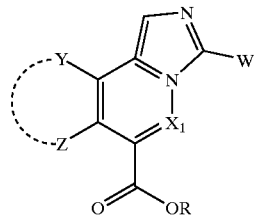

A-74 wherein Y, Z, $X_1$, and W are as defined for Formula I, and R is $C_1$–$C_6$ alkyl.

More preferred intermediate compounds are represented by formula A-75

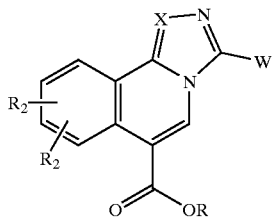

A-75 wherein X and $R_2$ are as defined in Formula I, $R_2$ is independently chosen at each occurrence, W is $W_2$, and R is $C_1$–$C_6$ alkyl.

Even more preferred are intermediates of Formula A-75 wherein $R_2$ is independently selected at each occurrence from the group consisting of $C_1$–$C_6$ alkyl, $C_1$–$C_6$ alkoxy, halogen, hydroxy, trifluoromethyl and trifluoromethoxy;

W is $W_2$; and

X is N or $CR_1$; wherein $R_1$ is selected from the group consisting of hydrogen, halogen, hydroxy, $C_1$–$C_6$ alkyl, and $C_1$–$C_6$ alkoxy.

Still another group of intermediates that are useful in preparing compounds of the instant invention are those of Formula A-76

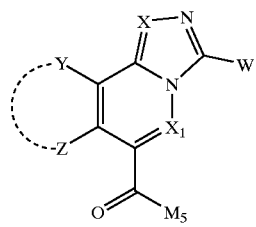

A-76 wherein Y, Z, X, $X_1$, and W are as defined for Formula I, and $M_5$ is hydroxy, $C_1$–$C_8$ alkyl, aryl($C_1$–$C_6$)alkyl, or —N($C_1$–$C_4$ alkyl) ($C_1$–$C_4$ alkoxy).

A more preferred group of intermediates of Formula A-76 are those of Formula A-77

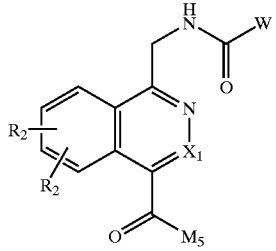

A-77 wherein $X_1$, $R_2$ and $M_5$ are as defined for formula 76; and W is $W_2$.

A preferred group of intermediates of Formula A-77 are those wherein $R_2$ is independently selected at each occurrence from the group consisting of $C_1$–$C_6$ alkyl, $C_1$–$C_6$ alkoxy, halogen, hydroxy, trifluoromethyl and trifluoromethoxy;

W is $W_2$; and $X_1$ is N or CH.

This invention relates to imidazoquinoline and triazoloquinoline derivatives and related compounds, preferred examples of which bind with high affinity to the benzodiazepine site of $GABA_A$ receptors, including human $GABA_A$ receptors. Preferred fused aryl substituted tetrahydroindazoles and related compounds that bind with high selectivity to the benzodiazepine site of $GABA_A$ receptors, including human $GABA_A$ receptors, are also included in this invention. Without wishing to be bound to any particular theory, it is believed that the interaction of the compounds of Formula I with the benzodiazepine site results in the pharmaceutical utility of these compounds.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/- agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g. attention deficit disorder (ADD), and attention deficit and hyperactivity disorder (ADHD).

The invention also provides pharmaceutical compositions comprising compounds of the invention, including packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5\text{-}HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer, s dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al. , J. Psychopharmacology (1997) 11(3) 211–218; Smith, et al., Am. J. Psychiatry (1998) 155(10) 1339–45; or Le, et al., Alcohol and Alcoholism (1996) 31 Suppl. 127–132. Also see, the discussion of the use of the $GABA_A$ receptor ligand 3-(5-methylisoxazol-3-yl)-6-(1-methyl-1,2,3-triazol-4-yl) methyloxy-1,2,4-triazolo[3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as Ro15-1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 50. The $GABA_A$ receptors used to determine in vitro binding may be obtained from a variety of sources, for example from preparations of rat cortex or from cells expressing cloned human $GABA_A$ receptors.

The present invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 51.

The $GABA_A$ receptor ligands provided by this invention and labeled derivatives thereof are also useful as standards and reagents in determining the ability of a potential pharmaceutical to bind to the $GABA_A$ receptor.

Labeled derivatives the $GABA_A$ receptor ligands provided by this invention are also useful as radiotracers for positron emission tomography (PET) imaging or for single photon emission computerized tomography (SPECT).

Definitions

If the compounds of the present invention have asymmetric centers, then this invention includes all of the optical isomers and mixtures thereof.

In addition, compounds with carbon-carbon double bonds may occur in Z- and E-forms, with all isomeric forms of the compounds being included in the present invention.

Compounds of Formula I may contain one or more asymmetric carbon atoms, so that the compounds can exist in different stereoisomeric forms. These compounds can be present as, for example, racemic mixtures, mixtures of diastereomers, and optically active forms including mixtures having one stereoisomer in enantiomeric excess and essentially pure stereoisomers, i.e., individual stereoisomers. In these latter situations, the single enantiomers can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malonic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

When any variable (e.g. $C_1$–$C_6$ alkyl, $C_1$–$C_8$ alkyl, $R_1$–$R_8$, W, X, Ar, G or Q) occurs more than one time in any formula herein, its definition on each occurrence is independent of its definition at every other occurrence.

As used herein, the term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like. Where the number of carbon atoms in the alkyl group is unspecified, the group is a $C_1$–$C_6$ alkyl groups.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy. Where the number of carbon atoms in the alkoxy group is unspecified the group is $C_1$–$C_6$ alkoxy.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, anthryl, phenanthryl, 1,2,3,4-tetrahydronaphthyl and biphenyl. Preferred examples of aryl groups include phenyl and naphthyl.

The terms "halogen" or "halo" indicate fluorine, chlorine, bromine, and iodine. Preferred halo groups are fluoro, chloro, and bromo. Most preferred are fluoro and chloro.

The term "heterocycloalkyl" refers to a non-aromatic ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, thiomorpholinyl, 1,1-thiomorpholinyl, and pyrolidinyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "hydroxyalkyl" as used herein, refers to a hydroxy group, attached to the parent molecular moiety through an alkyl group, as defined above.

As used herein, the term "oxo" refers to a doubly bonded oxygen atom forming carbonyl group with the carbon atom to which the oxygen is attached. Thus, where a ring contains one or more oxo groups, it is intended that that ring contains a carbonyl group in at least one of the ring positions.

This invention relates to heterocyclic derivatives that bind to the benzodiazepine site of $GABA_A$ receptors, including human $GABA_A$ receptors. A compound may bind to such sites with high affinity but not high specificity or a compound may bind with high selectivity but not high affinity.

The present invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvates, such as water, ethanol, mineral oil, vegetable oil, and dimethylsulfoxide.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate;

granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Representative illustrations of the preparation of compounds of Formula 1 in the present invention are given in Schemes 1–3.

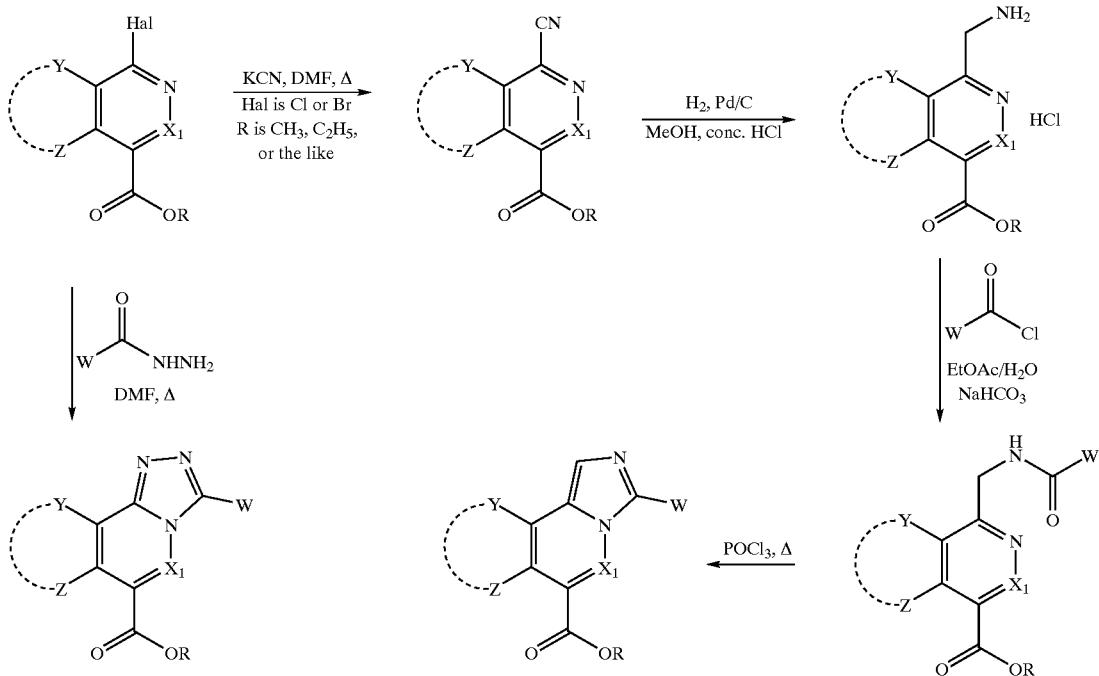

In Scheme I, W, $X_1$, X, and Y are as defined above for Formula 1 and R is $C_1$–$C_6$alkyl, MeOH is methanol, EtOAc is ethyl acetate, DMF is N,N-dimethylformamide, $POCl_3$ is phosphorus oxychloride, and conc. is concentrated. Heat, as used herein, means elevated temperature, such as, for example, about 40 to about 250° C.

In Scheme 2, X, $X_1$, Y, Z, W, W', J, $R_9$ and $R_{10}$ are as defined above for Formula 1, MeOH is methanol, BOP is benzotriazol-1-yloxytris(dimethylamino)-phosphoniumhexafluorophosphate, TEA is triethylamine, DMF is N,N-dimethylformamide, THF is tetrahydrofuran.

Heat, as used herein, means elevated temperature, such as, for example, about 40 to about 250° C.

Scheme 3

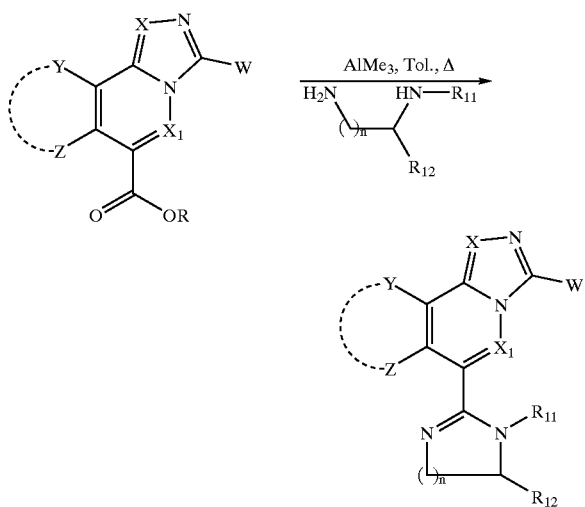

In Scheme 3, $X_1$, Y, Z, W, X, n, $R_{11}$ and $R_{12}$ are as defined above for Formula 1, Me is methyl, Tol is toluene and heat as used herein, means elevated temperature, such as, for example, about 40 to about 250° C.

Those skilled in the art will recognize that it may be necessary to utilize different solvents or reagents to achieve some of the above transformations.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of reactive functionalities may be necessary to achieve some of the above transformations. In general, such need for protecting groups, as well as the conditions necessary to attach and remove such groups, will be apparent to those skilled in the art of organic synthesis.

EXAMPLE 1

Preparation of 1-[(3-Phenylimidazo[5,1-a]isoguinolin-6-yl)carbonyl]piperidine

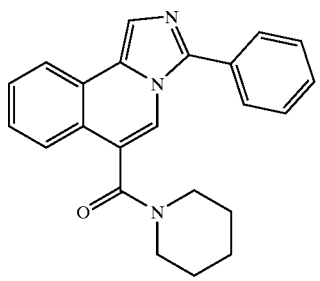

(1) 4-[(Dimethylamino)methylene]-1H-2-benzopyran-1,3(4H)-dione 100 ml of anhydrous DMF in a 1 liter round-bottomed, three necked flask (fitted with a drying tube containing drierite, and a 125 ml dropping funnel) is cooled in an ice-salt bath, and 31 ml of $POCl_3$ is subsequently added over a period of half an hour while stirring the DMF. The 125 ml dropping funnel is replaced with a 150 ml dropping funnel, and a solution of 54 g of homopthalic acid in 100 ml of DMF is added to the flask over a period of one hour at <10° C. The reaction mixture is then stirred at room temperature until a yellow paste was formed, and then poured into ice water. The solid is collected by filtration, washed with water and dried to give 54 g of the title compound as a yellow solid, m.p. 137–40° C.

(2) Methyl 1H-2-Benzopyran-1-oxo-4-carboxylate

Anhydrous HCl gas is continuously bubbled into a stirred solution of the product from part 1 (54 g) in 500 ml of methanol at slowly refluxing temperature for 6 hours. The reaction mixture is concentrated under vacuum. A $NaHCO_3$ solution is added to the residue. The solid was collected by filtration, washed and dried to yield 29.4 g of the title compound as a solid, m.p. 88–90° C.

(3) Methyl 1,2-Dihydro-1-oxo-4-isoquinolinecarboxylate

A mixture of the product from part 2 (29 g) and ammonium acetate (50 g) in 100 ml of acetic acid is stirred at 80°C. overnight, and then cooled and poured into water. The solid is collected by filtration, washed with water and dried to yield the title compound (25 g) as a white solid, m.p. 258–60° C.

(4) Methyl 1-Chloroisoquinoline-4-carboxylate

A mixture of the product from part 3 (12.5 g) in 50 ml of $POCl_3$ is stirred at 100° C. for about two hours then cooled and concentrated under vacuum. The residue is dissolved in 300 ml of $CHCl_3$, and the resulting solution is washed with aqueous $NaHCO_3$ and water, dried over $Na_2SO_4$, filtered and then concentrated to give the title compound, m.p. 53–55° C.

(5) Methyl 1-Isoquinolinecarbonitrile-4-carboxylate

A mixture of the product from part 4 (16 g) and potassium cyanide (5.4 g) in 50 ml of DMF was stirred at 90° C. for 4 hours. The mixture is cooled and poured into water. The solid is then collected by filtration, washed with water, and dried to give the title compound as a tan solid (11 g), m.p. 91–94° C.

(6) Methyl 1-Isoquinolinemethanamine-4-carboxylate dihydrochloride

A mixture of the product from part 5 (2 g) and 10% Pd on carbon (800 mg) in 50 ml of methanol containing 4 ml of conc. HCl is hydrogenated with a balloon of hydrogen for about half an hour. The mixture is filtered through celite and concentrated under vacuum to a solid. Recrystallization from EtOAc and methanol yields the title compound (1.8 g) as a white solid, m.p. 234–237° C. (dec).

(7) N-[(4-Methoxycarbonylisoquinolin-1-yl)methyl]benzamide

Benzoyl chloride (0.78 ml) is added dropwise to a stirred mixture of the product from part 6 (1.87 g) in 10 ml EtOAc and 10 ml of saturated aqueous $NaHCO_3$ solution. After stirring for 15 minutes, the layers are separated, the organic layer is washed with water, dried, filtered and concentrated to a solid. The solid is washed with hexanes and dried to yield 1.97 g of the desired product as a white solid, m.p. 140–142° C.

(8) Methyl 3-Phenylimidazo[5,1-a]isoquinolin-6-carboxylate

A mixture of the product from part 7 (1.97 g) in 10 ml of $POCl_3$ is stirred at 105° C. for two hours, then cooled and concentrated under vacuum. The residue is treated with EtOAc and washed with saturated aqueous $NaHCO_3$ solution and water. The organic solution is dried over $Na_2SO_4$, filtered and then concentrated to afford a solid. Recrystallization from 2-propanol yields the title compound as a yellow solid (0.7 g).

(9) 3-Phenylimidazo[5,1-a]isoquinolin-6-carboxylic Acid

A slurry of the product from part 8 (488 mg) and NaOH (226 mg) in 15 ml of methanol and 10 ml of water is stirred at 60° C. until a solution forms. The methanol is then evaporated in vacuo, and the remaining mixture is diluted with water. After adjusting the pH to 5–6 with 1N HCl, the solid is collected by filtration, washed with water and dried to give the title compound (450 mg) as a yellow solid, m.p. 187–90° C.

(10) 1-[(3-Phenylimidazo[5,1-a]isoquinolin-6-yl)carbonyl]-piperidine

A mixture of the product from part 9 (95 mg), BOP (220 mg), piperidine (56 mg) and TEA (67 mg) in 2 ml of DMF is stirred at room temperature for 18 hours. The mixture is added to aqueous NaHCO$_3$ solution and extracted with EtOAc. The organic layer is washed with brine and water, dried (Na$_2$SO$_4$), filtered and concentrated to afford a foam. Purification on a silica gel column, eluting with 5% methanol in methylene chloride, gives the title compound. $^1$H NMR (CDCl$_3$) δ 1.38–1.50 and 1.60–1.80 (6H, m), 3.18–3.36 (2H, m), 3.65–3.95 (2H, m), 7.40–7.60 (6H, m), 7.75 (2H, d), 7.95 (1H, s), 8.05 (1H, s), 8.10 (1H, d). The hydrochloride salt was prepared by treating the free base in EtOAc with a solution of hydrogen chloride in ether and collecting by filtration.

LC-MS data: HPLC: 1.93 min (HPLC method: Zorbax XDB-C$_{18}$ column, 4.6×30 mm, 3.5 μm particle size, 3 min gradient from 0 to 100% B with 0.5 min hold at 100% B. Solvent A: 95% H$_2$O-5%MeOH-0.05%TFA; Solvent B: 95%MeOH-5%H$_2$O-0.05%TFA). MS (ES$^+$): m/e 356 [M+H]$^+$.

EXAMPLES 2–40

The following compounds are prepared using procedures analogous to those of Example 1. The compounds of these examples have the general structure shown below:

where Q and W are defined in the following Table 1. LC-MS data are given as HPLC retention times (rt) and [M+H]$^+$. The HPLC retention times of Table 1 are obtained by the method given in Example 1.

TABLE 1

| Ex. No. | Q | W | Compound Name | HPLC rt (min) | [M + H]$^+$ |
|---|---|---|---|---|---|
| 2 | pyrrolidinyl carbonyl | phenyl | 1-[(3-Phenylimidazo[5,1-a]isoquinolin-6-yl)carbonyl]-pyrrolidine | 1.70 | 342 |
| 3 | 2-hydroxymethylpyrrolidinyl carbonyl | phenyl | (R)-1-[(3-Phenylimidazo[5,1-a]isoquinolin-6-yl)carbonyl]-2-hydroxymethyl-pyrrolidine | 1.47 | 372 |
| 4 | morpholinyl carbonyl | phenyl | 4-[(3-Phenylimidazo[5,1-a]isoquinolin-6-yl)carbonyl]-morpholine | 1.44 | 358 |
| 5 | 2,6-dimethylpiperidinyl carbonyl | phenyl | cis-1-[(3-Phenylimidazo[5,1-a]isoquinolin-6-yl)carbonyl]-2,6-dimethylpiperidine | 2.27 | 384 |
| 6 | thiomorpholinyl carbonyl | phenyl | 4-[(3-Phenylimidazo[5,1-a]isoquinolin-6-yl)carbonyl]-2,6-thiomorpholine | 1.84 | 374 |

TABLE 1-continued

| Ex. No. | Q | W | Compound Name | HPLC rt (min) | [M + H]+ |
|---|---|---|---|---|---|
| 7 | (acyl-2-methylpiperazine, N-methyl) | phenyl | 1-[(3-Phenylimidazo[5,1-a]isoquinolin-6-yl)carbonyl]-4-methylpiperazine | 0.94 | 371 |
| 8 | (acyl-3,5-dimethylpiperazine) | phenyl | cis-1-[(3-Phenylimidazo[5,1-a]isoquinolin-6-yl)carbonyl]-3,5-dimethylpiperazine | 1.13 | 385 |
| 9 | C(O)N(CH₃)₂ | phenyl | 1-[(3-Phenylimidazo[5,1-a]isoquinolin-6-yl)carbonyl]-N,N-dimethylamine | 1.40 | 316 |
| 10 | C(O)N(Et)₂ | phenyl | 1-[(3-Phenylimidazo[5,1-a]isoquinolin-6-yl)carbonyl]-N,N-diethylamine | 1.80 | 344 |
| 11 | acyl-pyrrolidine | 4-fluorophenyl | 1-{[3-(4-Fluorophenyl)-imidazo[5,1-a]isoquinolin-6-yl]carbonyl}pyrrolidine | 1.80 | 360 |
| 12 | acyl-2-hydroxymethylpyrrolidine | 4-fluorophenyl | (R)-1-{[3-(4-Fluorophenyl)-imidazo[5,1-a]isoquinolin-6-yl]carbonyl}-2-hydroxymethyl-pyrrolidine | 1.63 | 390 |
| 13 | acyl-piperidine | 4-fluorophenyl | 1-{[3-(4-Fluorophenyl)-imidazo[5,1-a]isoquinolin-6-yl]carbonyl}piperidine | 2.08 | 374 |
| 14 | acyl-pyrrolidine | 2-fluorophenyl | 1-{[3-(2-Fluorophenyl)-imidazo[5,1-a]isoquinolin-6-yl]carbonyl}pyrrolidine | 1.97 | 360 |
| 15 | acyl-2-hydroxymethylpyrrolidine | 2-fluorophenyl | (R)-1-{[3-(2-Fluorophenyl)-imidazo[5,1-a]isoquinolin-6-yl]carbonyl)-2-hydroxymethyl-pyrrolidine | 1.73 | 390 |

TABLE 1-continued

| Ex. No. | Q | W | Compound Name | HPLC rt (min) | [M + H]+ |
|---|---|---|---|---|---|
| 16 | 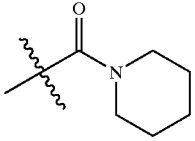 | 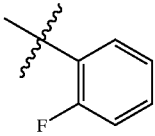 | 1-{[3-(2-Fluorophenyl)-imidazo[5,1-a]isoquinolin-6-yl]carbonyl}piperidine | 2.22 | 374 |
| 17 | 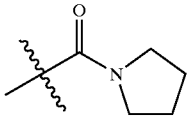 | 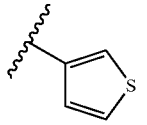 | 1-{[3-(Thien-3-yl)imidazo[5,1-a]isoquinolin-6-yl]carbonyl}-pyrrolidine | 1.61 | 348 |
| 18 | 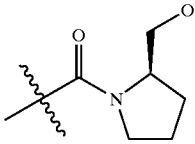 | 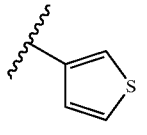 | (R)-1-{[3-(Thien-3-yl)imidazo[5,1-a]isoquinolin-6-yl]carbonyl}-2-hydroxymethyl-pyrrolidine | 1.40 | 378 |
| 19 | 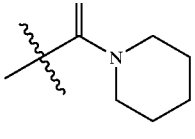 | 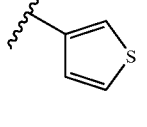 | 1-{[3-(Thien-3-yl)imidazo]5,1-a]isoquinolin-6-yl]carbonyl}-piperidine | 1.89 | 362 |
| 20 | 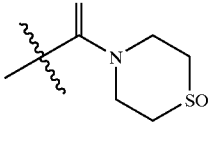 | 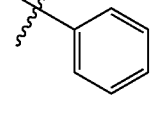 | 4-[(3-Phenylimidazo[5,1-a]isoquinolin-6-yl)carbonyl]-1,1-dioxido-thiomorpholine | 1.24 | 406 |
| 21 | 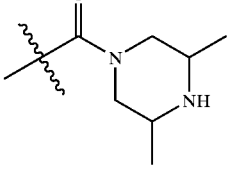 | 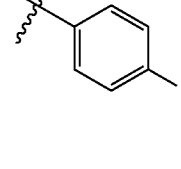 | cis-1-{[3-(4-Fluorophenyl)-imidazo[5,1-a]isoquinolin-6-yl]carbonyl}-3,5-dimethyl-piperazine | 1.22 | 402 |
| 22 | 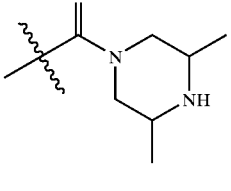 | 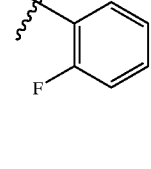 | cis-1-{[3-(2-Fluorophenyl)-imidazo[5,1-a]isoquinolin-6-yl]carbonyl}}-3,5-dimethyl-piperazine | 1.37 | 402 |
| 23 | 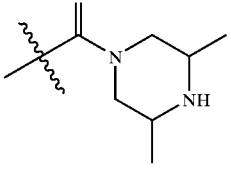 | 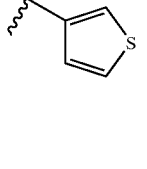 | cis-1-{[3-(Thien-3-yl)imidazo[5,1-a]isoquinolin-6-yl]carbonyl}-}-3,5-dimethyl-piperazine | 1.04 | 391 |
| 24 | 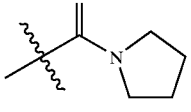 | 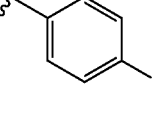 | 1-{[3-(4-Chlorophenyl)-imidazo[5,1-a]isoquinolin-6-yl]carbonyl}pyrrolidine | 2.10 | 376 |

TABLE 1-continued

| Ex. No. | Q | W | Compound Name | HPLC rt (min) | [M + H]+ |
|---|---|---|---|---|---|
| 25 | 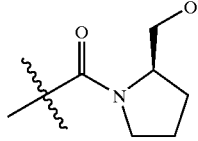 | 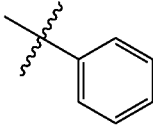 | (R)-1-{[3-(4-Chlorophenyl)-imidazo[5,1-a]isoquinolin-6-yl]carbonyl}-2-hydroxymethyl-pyrrolidine | 1.92 | 406 |
| 26 | 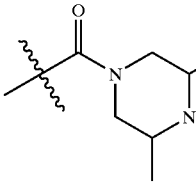 | 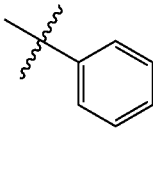 | cis-1-{[3-(4-Chlorophenyl)-imidazo[5,1-a]isoquinolin-6-yl]carbonyl}-3,5-dimethyl-piperazine | 1.54 | 419 |
| 27 | 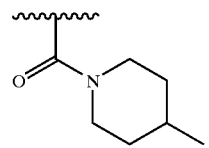 | 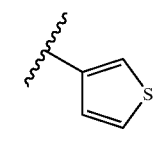 | 1-{[3-(Thien-3-yl)imidazo[5,1-a]isoquinolin-6-yl]carbonyl}-4-methyl piperidine | | 376 |
| 28 | 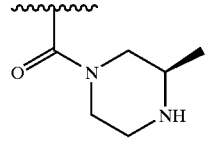 | 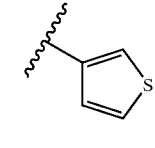 | (R)-1-{[3-(Thien-3-yl)imidazo[5,1-a]isoquinolin-6-yl]carbonyl}-3-methyl-piperazine | | 377 |
| 29 | 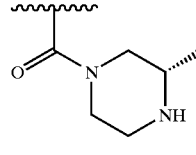 | 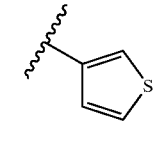 | (S)-1-{[3-(Thien-3-yl)imidazo[5,1-a]isoquinolin-6-yl]carbonyl}-3-methyl-piperazine | | 377 |
| 30 | 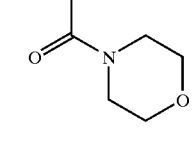 | 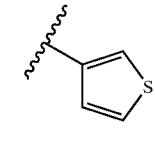 | 4-{[3-(Thien-3-yl)imidazo[5,1-a]isoquinolin-6-yl]carbonyl}morpholine | | 364 |
| 31 | 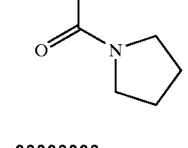 | 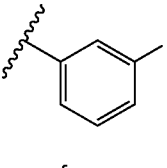 | 1-{[3-(3-Fluorophenyl)-imidazo[5,1-a]isoquinolin-6-yl]carbonyl}pyrrolidine | | 360 |
| 32 | 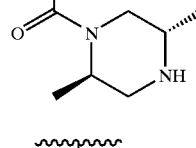 | 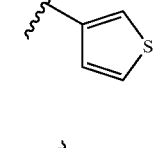 | cis-1-{[3-(Thien-3-yl)imidazo[5,1-a]isoquinolin-6-yl]carbonyl}-2,5-dimethylpiperazine | | 391 |
| 33 | 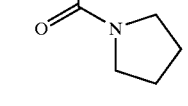 | 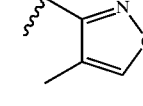 | 1-{[3-(4-Methylisoxazol-3-yl)-imidazo[5,1-a]isoquinolin-6-yl]carbonyl}pyrrolidine | | 347 |

TABLE 1-continued

| Ex. No. | Q | W | Compound Name | HPLC rt (min) | [M + H]+ |
|---|---|---|---|---|---|
| 34 | (morpholine carbonyl) | 3-fluorophenyl | 4-{[3-(3-Fluorophenyl)-imidazo[5,1-a]isoquinolin-6-yl]carbonyl}morpholine | | 376 |
| 35 | (R)-2-hydroxymethylpyrrolidine carbonyl | 3-fluorophenyl | (R)-1-{[3-(3-Fluorophenyl)-imidazo[5,1-a]isoquinolin-6-yl]carbonyl}-2-hydroxymethyl-pyrrolidine | | 390 |
| 36 | piperidine carbonyl | 3-fluorophenyl | 1-{[3-(3-Fluorophenyl)-imidazo[5,1-a]isoquinolin-6-yl]carbonyl}piperidine | | 374 |
| 37 | (S)-3-methylpiperazine carbonyl | phenyl | S-1-[3-(3-Phenylimidazo[5,1-a]isoquinolin-6-yl)carbonyl]-3-methylpiperazine | | 371 |
| 38 | (S)-3-methylpiperazine carbonyl | 2-fluorophenyl | (S)-1-{[3-(2-Fluorophenyl)-imidazo[5,1-a]isoquinolin-6-yl]carbonyl}-3-methylpiperazine | | 389 |
| 39 | (S)-3-methylpiperazine carbonyl | 4-fluorophenyl | (S)-1-{[3-(4-Fluorophenyl)-imidazo[5,1-a]isoquinolin-6-yl]carbonyl}-3-methylpiperazine | | 389 |
| 40 | homopiperazine carbonyl (azepane) | 4-methoxyphenyl | (S)-1-{[3-(4-Methoxyphenyl)-imidazo[5,1-a]isoquinolin-6-yl]carbonyl}-homopiperazine | | 400 |

EXAMPLE 41

Preparation of 1-[(3-Phenyl-1,2,4-triazolo[3,4-a]isoquinoline-6-yl)carbonyl]piperidine

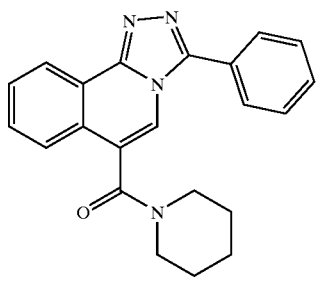

(1) Methyl 3-Phenyl-1,2,4-triazolo[3,4-a]isoquinoline-6-carboxylate

A mixture of methyl 1-Chloroisoquinoline-4-carboxylate, prepared essentially according to procedures described in Example 1, part 4, (293 mg) and benzoic hydrazide (192 mg) in 8 ml of DMF is stirred at 100° C. overnight. The mixture is cooled and poured into water. The solid is then collected by filtration and dried to give the title compound as a solid (258 mg). LC-MS data for the title compound: HPLC: 2.34 min. MS (ES+) m/e 304 [M+H]+. (The HPLC retention time is obtained by the method of Example 1).

(2) 3-Phenyl-1,2,4-triazolo[3,4-a]isoquinoline-6-carboxylic Acid

This compound is prepared using the procedure described in Example 1, part 9 with the product of part 1 of this example being used as the starting material.

(3) 1-[(3-Phenyl-1,2,4-triazolo[3,4-a]isoquinoline-6-yl)carbonyl]piperidine

This compound is prepared essentially using the procedure described in Example 1, part 10 with the product of part 2 of this example being used as the starting material. Data for the title compound: $^1$H NMR (CDCl$_3$) δ 1.38–2.00 (6H, m), 3.16–3.36 (2H, m), 3.65–3.95 (2H, m), 7.50–7.86 (8H, m), 8.05 (1H, s), 8.82 (1H, d).

LC-MS data: HPLC: 2.13 min. MS (ES$^+$) m/e 357 [M+H]$^+$. (The HPLC retention time is obtained by the method given in Example 1).

EXAMPLES 42–45

The following compounds are prepared by procedures analogous to those of Example 41. These compounds are represented by the general structure shown below:

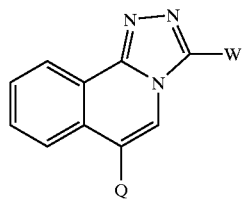

where Q and W are defined in Table 2. HPLC-MS data are given as HPLC retention times (Tr) and [M+H]$^+$. The HPLC retention time is obtained by the method of Example 1.

EXAMPLE 46

Preparation of 3-Phenyl-6-(S-5,6,7,7a-tetrahydro-1H-pyrrolo[1,2-c]imidazole-3-yl-)-imidazo[5,1-a]isoquinoline

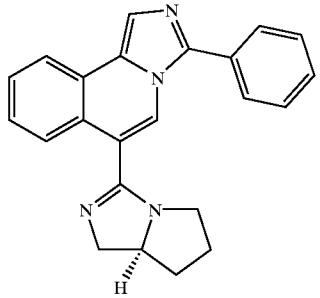

A solution of trimethylaluminum in anhydrous toluene (1M, 2.5 ml) is added dropwise to a stirred solution of S-2-(aminomethyl) pyrrolidine (250 mg) in 10 ml of anhydrous toluene. The mixture is then slowly warmed to 80° C. and stirred for one hour. After cooling to room temperature, methyl 3-phenylimidazo[5,1-a]isoquinolin-6-carboxylate (prepared essentially according to procedures described in Example 1, part 8, 97 mg) was added in one portion. The reaction mixture is heated at reflux for 12 hours under nitrogen. After cooling, the solution is treated dropwise with 5 ml of water, diluted with 10 ml of methanol and 10 ml of

TABLE 2

| Ex. No. | Q | W | Compound Name | HPLC (Tr) (min) | [M + H]$^+$ |
|---|---|---|---|---|---|
| 42 | | | 1-[(3-Phenyl-1,2,4-triazolo[3,4-a]isoquinoline-6-yl)carbonyl]pyrrolidine | 1.93 | 343 |
| 43 | | | (R)-1-[(3-Phenyl-1,2,4-triazolo[3,4-a]isoquinoline-6-yl)carbonyl]-2-hydroxymethyl-pyrrolidine | 1.73 | 373 |
| 44 | | | 4-[(3-Phenyl-1,2,4-triazolo[3,4-a]isoquinoline-6-yl)carbonyl]morpholine | 1.74 | 359 |
| 45 | | | cis-1-[(3-Phenyl-1,2,4-triazolo[3,4-a]isoquinoline-6-yl)carbonyl]-3,5-dimethylpiperazine | 1.37 | 386 | methylene chloride, and refluxed for another 15 minutes. After filtration over celite and Na$_2$SO$_4$, and solvent evaporation, the residue is mixed with EtOAc and water. The organic layer is then separated, washed with brine, dried (Na$_2$SO$_4$), filtered and concentrated in vacuo. The residue is purified on a silica gel column, eluting with 5% methanol in methylene chloride to yield the titled compound. $^1$H NMR (CDCl$_3$) δ 1.40–2.05 (4H, m), 3.00–3.20 (2H, m), 3.80–4.20 (3H, m), 7.40–7.62 (5H, m), 7.80 (2H, d), 7.95 (1H, s), 8.08 (1H, d), 8.35 (1H, d), 8.40 (1H, s). LC-MS data: HPLC: 1.51 min. MS (ES$^+$) m/e 353 [M+H]$^+$. The HPLC retention time was obtained by the method of Example 1.

EXAMPLE 47

Preparation of 1-[(3-Phenyl-1,2,4-triazolo[3,4-a]isoquinoline-6-yl)carbonyl]piperidine

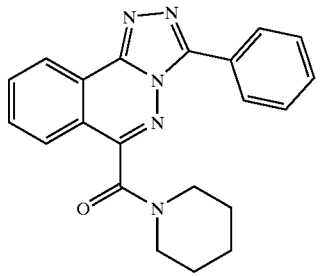

(1) 3-Phenyl-1,2,4-Triazolo[3,4-a]phthalazine-6-carboxylic Acid

A mixture of 6-Chloro-3-phenyl-1,2,4-Triazolo[3,4-a]phthalazine (2.0 g, prepared according to procedures described in Zh. Org. Khim. (1975), 11(7), 1570–2 and J. Med. Chem. (1988),31(6), 1115–23.) and copper cynaide (2.0 g) in 50 ml of DMSO is stirred at 140° C. overnight. The mixture is cooled, poured into water and extracted with methylene chloride. The organic layer is washed with water, dried over Na$_2$SO$_4$ and concentrated to give a tan solid which is then dissolved in 50 mL of methanol. The resulting solution is saturated with HCl gas and the mixture is stirred at room temperature overnight. 20 mL of water and 1 mL of 10 N NaOH solution are added, the resulting mixture is then heated under reflux for 4 hours. The methanol is then evaporated in vacuo, and the remaining mixture is diluted with water. After adjusting the pH to 4–5 with 1N HCl, the solid is collected by filtration, and dried to give the title compound as a solid.

(2) 1-[(3-Phenyl-1,2,4-triazolo[3,4-al]phthalazine-6-yl)carbonyl]piperidine

This compound is prepared essentially using the procedure described in Example 1, part 10 with the product of part 1 of this example being used as the starting material.

EXAMPLE 48

Preparation of Radiolabeled Probe Compounds of the Invention

The compounds of the invention may be prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably $^{125}$I). Such radiolabeled probes are conveniently synthesized by a radio-isotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

EXAMPLE 49

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

EXAMPLE 50

Binding Assay

The high affinity and high selectivity of compounds of this invention for the benzodiazepine site of the GABA$_A$ receptor is demonstrated using the following binding assay. This assay is carried out essentially as described by Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20 ° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations contained 100 µl of tissue homogenate, 100 µl of radioligand, (0.5 nM $^3$H-Ro15-1788 [$^3$H-Flumazenil], specific activity 80 Ci/mmol), and test compound or control (see below), and are brought to a total volume of 500 µl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 ($^3$H-Flumazenil) with 10 µM Diazepam (Research Biochemicals International, Natick, Mass.). Data are collected in triplicate, averaged, and percent inhibition of total specific binding (Total Specific Binding=Total−Nonspecific) is calculated for each compound.

A competition binding curve is obtained with up to 11 points spanning the compound concentration range from $10^{-12}$M to $10^{-5}$M obtained per curve by the method described above for determining percent inhibition. $K_i$ values are calculated according the Cheng-Prussof equation. Each of the compounds shown and described in Examples 1 through 46, and tested in this assay was found to have a $K_i$ of <1 μM.

EXAMPLE 51

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

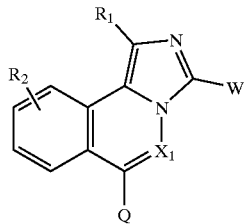

or a pharmaceutically acceptable salt thereof, wherein:

$R_1$ is hydrogen, halogen, hydroxy, cyano, nitro, amino, $C_1$–$C_6$ alkyl, $C_1$–$C_6$alkoxy, trifluoromethyl, trifluoromethoxy, —NH($C_1$–$C_6$alkyl), —N($C_1$–$C_6$alkyl)($C_1$–$C_6$alkyl), or $H_2N$($C_1$–$C_6$alkylene);

$X_1$ is CH or a carbon atom substituted with $C_1$–$C_6$ alkyl;

$R_2$ represents 0 to 4 groups independently chosen at each occurrence from halogen, hydroxy, cyano, nitro, amino, $C_1$–$C_6$ alkyl, $C_1$–$C_6$alkoxy, trifluoromethyl, trifluoromethoxy, —NH($C_1$–$C_6$alkyl), —N($C_1$–$C_6$alkyl)($C_1$–$C_6$alkyl), or $H_2N$($C_1$–$C_6$alkylene);

W is aryl or heteroaryl, each of which is optionally substituted with one or more groups $R_A$, wherein each $R_A$ is independently i) halogen, hydroxy, cyano, nitro, amino, $C_1$–$C_6$alkoxy, trifluoromethyl, trifluoromethoxy, —$SO_2NH_2$, —$SO_2NH(C_1$–$C_8$ alkyl), —$SO_2N(C_{1-8}$ alkyl)($C_1$–$C_8$ alkyl), —NH($C_1$–$C_8$ alkyl), —N($C_1$–$C_8$ alkyl)($C_{1-8}$ alkyl), —N($C_1$–$C_8$ alkyl)CO($C_1$–$C_8$ alkyl), —N($C_1$–$C_8$ alkyl)$CO_2$($C_1$–$C_8$ alkyl), —$CONH_2$, —CONH($C_1$–$C_8$ alkyl), —CON($C_1$–$C_8$ alkyl)($C_1$–$C_8$ alkyl), —$CO_2$($C_1$–$C_8$ alkyl), —S($C_1$–$C_8$ alkyl), —SO($C_1$–$C_8$ alkyl), or —$SO_2$($C_1$–$C_8$ alkyl);

ii) aryl or heteroaryl, each of which is optionally substituted with one or two groups independently selected from halogen, hydroxy, cyano, nitro, amino, $C_1$–$C_6$ alkyl, $C_1$–$C_6$alkoxy, trifluoromethyl, trifluoromethoxy, —NH($C_1$–$C_6$alkyl), —N($C_1$–$C_6$alkyl)($C_1$–$C_6$alkyl), or $H_2N$($C_1$–$C_6$alkylene);

iii) $C_1$–$C_8$alkyl, $C_2$–$C_8$alkenyl, $C_2$–$C_8$ alkynyl, $C_3$–$C_8$cycloalkyl, $C_3$–$C_8$cycloalkyl($C_1$–$C_3$ alkyl), $C_3$–$C_8$cycloalkenyl, each of which is unsubstituted or substituted by one or more substituents independently selected from hydroxy, oxo, halogen, $C_1$–$C_6$alkoxy, —$CONH_2$, —$CONHC_1$–$C_6$alkyl, —CON($C_1$–$C_6$alkyl)($C_1$–$C_6$alkyl), —COOH, and —$CO_2C_1$–$C_6$alkyl; or iv) $NR_4R_5$, wherein $R_4$, $R_5$ and the nitrogen to which they are attached form a monocyclic or bicyclic ring optionally containing one or more of oxo, O, S, SO, SO₂, or NR₆ wherein R₆ is hydrogen, $C_1$–$C_6$alkyl, or Ar—($C_1$–$C_6$alkyl) where
Ar is aryl or heteroaryl, each of which is optionally substituted with one or two groups independently selected from halogen, hydroxy, cyano, nitro, amino, $C_1$–$C_6$ alkyl, $C_1$–$C_6$alkoxy, trifluoromethyl, trifluoromethoxy, mono or di($C_1$–$C_6$)alkylamino, and amino($C_1$–$C_6$)alkyl; and Q is selected Formulas III, IV and V:

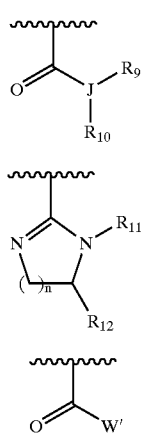

Formula III

Formula IV

Formula V wherein:
J is N or $C_1$–$C_8$ alkylene; and
$R_9$ and $R_{10}$ are independently hydrogen, $C_1$–$C_8$ alkyl, or $Ar_1$, wherein $Ar_1$ is aryl or heteroaryl, each of which may be substituted with one or two of $R_B$, where each $R_B$ independently carries the definition of $R_A$; or
$R_9$, $R_{10}$ and the atom to which they are attached form a 4- to 8-membered monocyclic or bicyclic ring optionally containing one or more double bonds or one or more of oxo, O, S, SO, SO₂, or N—$R_8$ wherein $R_8$ is hydrogen, $C_1$–$C_8$ alkyl, or $Ar_1$—($C_1$–$C_8$ alkyl); wherein $Ar_1$ is optionally substituted with one or two of $R_B$, where each $R_B$ independently carries the definition of $R_A$; and wherein the monocyclic or bicyclic ring is optionally substituted with $C_1$–$C_6$ alkyl or hydroxy($C_1$–$C_6$)alkyl;
$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and
$R_{12}$ is selected from the group consisting of hydrogen, $C_1$–$C_8$ alkyl, and $C_1$–$C_8$ alkoxy; or
$R_{11}$ and $R_{12}$ together with the atoms to which they are attached form a 5–8 membered monocyclic ring which is optionally substituted with one or more of halogen, hydroxy, cyano, nitro, amino, $C_1$–$C_6$ alkyl, $C_1$–$C_6$alkoxy, trifluoromethyl, trifluoromethoxy, —NH($C_1$–$C_6$alkyl), —N($C_1$–$C_6$alkyl) ($C_1$–$C_6$alkyl), or H₂N($C_1$–$C_6$alkylene); and
n is 1, 2, 3, or 4; and
W'
(i) independently carries the same definition as W;
(ii) represents —OR where R is $C_1$–$C_8$ alkyl or aryl($C_1$–$C_6$)alkyl; or
(iii) is $M_5$ where $M_5$ is hydroxy, $C_1$–$C_8$ alkyl, aryl ($C_1$–$C_6$)alkyl or —N($C_1$–$C_4$ alkyl) ($C_1$–$C_4$ alkoxy).

2. A compound according to claim 1 of the formula

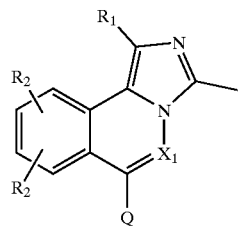

wherein each $R_1$, Q, and $X_1$ are defined as in claim 1, $R_2$ represents 0 to 2 groups independently chosen at each occurrence from halogen, hydroxy, cyano, nitro, amino, $C_1$–$C_6$ alkyl, $C_1$–$C_6$alkoxy, trifluoromethyl, trifluoromethoxy, —NH($C_1$–$C_6$alkyl), —N($C_1$–$C_6$alkyl) ($C_1$–$C_6$alkyl), or H₂N ($C_1$–$C_6$alkylene); and W is phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl or benzopyrazolyl, each of which is unsubstituted or substituted with one or more substituents independently selected from the group consisting of:
halogen, hydroxy, cyano, nitro, amino, $C_1$–$C_8$alkyl, $C_1$–$C_6$alkoxy, trifluoromethyl, trifluoromethoxy, —SO₂NH₂, —SO₂NH($C_1$–$C_8$ alkyl), —SO₂N($C_{1-8}$ alkyl) ($C_1$–$C_8$ alkyl), —NH($C_1$–$C_8$ alkyl), —N($C_1$–$C_8$ alkyl) ($C_{1-8}$ alkyl), —N($C_1$–$C_8$ alkyl) CO($C_1$–$C_8$ alkyl), —N($C_1$–$C_8$ alkyl)CO₂($C_1$–$C_8$ alkyl), —CONH₂, —CONH($C_1$–$C_8$ alkyl), —CON ($C_1$–$C_8$ alkyl) ($C_1$–$C_8$ alkyl), —CO₂($C_1$–$C_8$ alkyl), —S($C_1$–$C_8$ alkyl), —SO($C_1$–$C_8$ alkyl), —SO₂ ($C_1$–$C_8$ alkyl) and phenyl.

3. A compound according to claim 2 wherein W is phenyl, naphthyl, thienyl, pyridyl, pyrazinyl, pyrimidyl, imidazolyl, isoxazolyl, furanyl, thiazolyl, benzothiazolyl, pyrrolyl, pyrazolyl or benzopyrazolyl, each of which is unsubstituted or substituted with one or more substituents independently selected from the group consisting of:
halogen, hydroxy, cyano, nitro, amino, $C_1$–$C_8$alkyl, $C_1$–$C_6$alkoxy, trifluoromethyl, trifluoromethoxy, —SO₂NH₂, —SO₂NH($C_1$–$C_8$ alkyl), —SO₂N($C_{1-8}$ alkyl) ($C_1$–$C_8$ alkyl), —NH($C_1$–$C_8$ alkyl), —N($C_1$–$C_8$ alkyl) ($C_{1-8}$ alkyl), —N($C_1$–$C_8$ alkyl)CO($C_1$–$C_8$ alkyl), —N($C_1$–$C_8$ alkyl)CO₂($C_1$–$C_8$ alkyl), —CONH₂, —CONH($C_1$–$C_8$ alkyl), —CON($C_1$–$C_8$ alkyl) ($C_1$–$C_8$ alkyl), —CO₂($C_1$–$C_8$ alkyl), —S($C_1$–$C_8$ alkyl), —SO ($C_1$–$C_8$ alkyl), —SO₂($C_1$–$C_8$ alkyl) and phenyl.

4. A compound according to claim 3, wherein
$R_2$ is independently selected at each occurrence from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V:

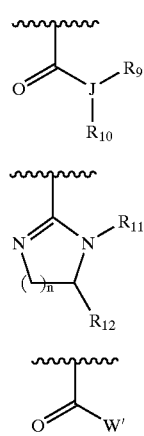

Formula III

Formula IV

Formula V wherein:
J is N or $C_1$–$C_8$ alkylene; and
$R_9$ and $R_{10}$ are independently hydrogen, $C_1$–$C_8$ alkyl; or
$R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_6$)alkyl;
$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and
$R_{12}$ is selected from the group consisting of hydrogen, $C_1$–$C_8$ alkyl, and $C_1$–$C_8$ alkoxy; or
$R_{11}$ and $R_{12}$ together with the atoms to which they are attached form a 5–8 membered monocyclic ring, which is optionally substituted with $C_1$–$C_6$alkyl; and
n is 1, 2, 3, or 4;
W' phenyl, pyridyl, or naphthyl; and
W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

5. A compound according to claim 3, wherein $R_1$ is hydrogen or $C_1$–$C_6$ alkyl.

6. A compound according to claim 5, wherein
W is phenyl, naphthyl, thienyl, pyridyl, pyrazinyl, pyrimidyl, imidazolyl, isoxazolyl, furanyl, thiazolyl, benzothiazolyl, pyrrolyl, pyrazolyl or benzopyrazolyl, each of which is unsubstituted or substituted with one or more substituents independently selected from the group consisting of:
halogen, hydroxy, cyano, nitro, amino, $C_1$–$C_8$alkyl, $C_1$–$C_6$alkoxy, trifluoromethyl, trifluoromethoxy, —$SO_2NH_2$, —$SO_2NH(C_1$–$C_8$ alkyl), —$SO_2N(C_{1-8}$ alkyl) ($C_1$–$C_8$ alkyl), —NH($C_1$–$C_8$ alkyl), —N($C_1$–$C_8$ alkyl) ($C_{1-8}$ alkyl), —N($C_1$–$C_8$ alkyl) CO($C_1$–$C_8$ alkyl), —N($C_1$–$C_8$ alkyl)$CO_2$($C_1$–$C_8$ alkyl), —$CONH_2$, —CONH($C_1$–$C_8$ alkyl), —CON($C_1$–$C_8$ alkyl) ($C_1$–$C_8$ alkyl), —$CO_2$($C_1$–$C_8$ alkyl), —S($C_1$–$C_8$ alkyl), —SO($C_1$–$C_8$ alkyl), —$SO_2$($C_1$–$C_8$ alkyl) and phenyl.

7. A compound according to claim 6, wherein
$R_2$ is independently selected at each occurrence from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V wherein:
J is N or $C_1$–$C_8$ alkylene; and
$R_9$ and $R_{10}$ are independently hydrogen, $C_1$–$C_8$ alkyl; or
$R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_6$)alkyl;
$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and
$R_{12}$ is selected from the group consisting of hydrogen, $C_1$–$C_8$ alkyl, and $C_1$–$C_8$ alkoxy; or
$R_{11}$ and $R_{12}$ together with the atoms to which they are attached form a 5–8 membered monocyclic ring, which is optionally substituted with $C_1$–$C_6$alkyl; and
n is 1, 2, 3, or 4;
W' phenyl, pyridyl, or naphthyl; and
W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

8. A compound according to claim 2, wherein where $R_1$ is hydrogen or $C_1$–$C_6$ alkyl.

9. A compound according to claim 3, wherein $R_1$ is hydrogen or $C_1$–$C_6$ alkyl.

10. A compound according to claim 9, wherein $R_2$ is independently selected at each occurrence from the group consisting of $C_1$–$C_6$ alkyl, $C_1$–$C_6$ alkoxy, halogen, hydroxy, trifluoromethyl and trifluoromethoxy;

Q is selected from the group consisting of Formulas III, IV and V wherein:
J is N or $C_1$–$C_8$ alkylene; and
$R_9$ and $R_{10}$ are independently hydrogen, $C_1$–$C_8$ alkyl; or
$R_9$, $R_{10}$ and the atom to which they are attached form a 4- to 8-membered monocyclic or bicyclic ring, which may contain one or more double bonds or one or more of oxo, O, S, SO, $SO_2$, or N—$R_8$ wherein $R_8$ is hydrogen, $C_1$–$C_8$ alkyl; wherein the monocyclic or bicyclic ring is optionally substituted with $C_1$–$C_6$ alkyl or hydroxy($C_1$–$C_6$)alkyl;
$R_{11}$ is selected from the group consisting of hydrogen, $C_1$–$C_8$ alkyl, $C_1$–$C_8$ alkanoyl, aryl($C_1$–$C_6$)alkyl, and aryl($C_1$–$C_6$)alkanoyl; and
$R_{12}$ is selected from the group consisting of hydrogen, $C_1$–$C_8$ alkyl, and $C_1$–$C_8$ alkoxy; or
$R_{11}$ and $R_{12}$ together with the atoms to which they are attached form a 5–8 membered monocyclic ring, which is optionally substituted with $C_1$–$C_6$ alkyl; and
n is 1, 2, 3, or 4;
W' phenyl, pyridyl, or naphthyl; and
W is phenyl, thienyl, isoxazolyl, or pyridyl, each of which is unsubstituted or substituted with one or more substituents independently selected from the group consisting of halogen, $C_1$–$C_6$ alkyl, $C_1$–$C_6$ alkoxy, trifluoromethyl, trifluoromethoxy, and hydroxy.

11. A compound according to claim 1, which is:
1-[(3-Phenylimidazo[5,1-a]isoquinolin-6-yl)carbonyl]piperidine.

12. A compound according to claim 1, which is: 1-[(3-Phenylimidazo[5,1-a]isoquinolin-6-yl)carbonyl]pyrrolidine.

13. A compound according to claim 1, which is: (R)-1-[(3-Phenylimidazo[5,1-a]isoquinolin-6-yl)carbonyl]-2-hydroxymethyl-pyrrolidine.

14. A compound according to claim 1, which is: 4-[(3-Phenylimidazo[5,1-a]isoquinolin-6-yl)carbonyl]morpholine.

15. A compound according to claim 1, which is: cis-1-[(3-Phenylimidazo[5,1-a]isoquinolin-6-yl)carbonyl]-2,6-dimethylpiperidine.

16. A compound according to claim 1, which is: 4-[(3-Phenylimidazo[5,1-a]isoquinolin-6-yl)carbonyl]-thiomorpholine.

17. A compound according to claim 1, which is: 1-[(3-Phenylimidazo[5,1-a]isoquinolin-6-yl)carbonyl]-4-methylpiperazine.

18. A compound according to claim 1, which is: cis-1-[(3-Phenylimidazo[5,1-a]isoquinolin-6-yl)carbonyl]-3,5-dimethylpiperazine.

19. A compound according to claim 1, which is: 1-[(3-Phenylimidazo[5,1-a]isoquinolin-6-yl)carbonyl]-N,N-dimethylamine.

20. A compound according to claim 1, which is: 1-[(3-Phenylimidazo[5,1-a]isoquinolin-6-yl)carbonyl]-N,N-diethylamine.

21. A compound according to claim 1, which is: 1-{[3-(4-Fluorophenyl)-imidazo[5,1-a]isoquinolin-6-yl]carbonyl}pyrrolidine.

22. A compound according to claim 1, which is: (R)-1-{[3-(4-Fluorophenyl)-imidazo[5,1-a]isoquinolin-6-yl]carbonyl}-2-hydroxymethyl-pyrrolidine.

23. A compound according to claim 1, which is: 1-{[3-(4-Fluorophenyl)-imidazo[5,1-a]isoquinolin-6-yl]carbonyl}piperidine.

24. A compound according to claim 1, which is: 1-{[3-(2-Fluorophenyl)-imidazo[5,1-a]isoquinolin-6-yl]carbonyl}pyrrolidine.

25. A compound according to claim 1, which is: (R)-1-{[3-(2-Fluorophenyl)-imidazo[5,1-a]isoquinolin-6-yl]carbonyl}-2-hydroxymethyl-pyrrolidine.

26. A compound according to claim 1, which is: 1-{[3-(2-Fluorophenyl)-imidazo[5,1-a]isoquinolin-6-yl]carbonyl}piperidine.

27. A compound according to claim 1, which is: 1-{[3-(Thien-3-yl)imidazo[5,1-a]isoquinolin-6-yl]carbonyl}pyrrolidine.

28. A compound according to claim 1, which is: (R)-1-{[3-(Thien-3-yl)imidazo[5,1-a]isoquinolin-6-yl]carbonyl}-2-hydroxymethylpyrrolidine.

29. A compound according to claim 1, which is: 1-{[3-(Thien-3-yl)imidazo[5,1-a]isoquinolin-6-yl]carbonyl}piperidine.

30. A compound according to claim 1, which is: 4-[(3-Phenylimidazo[5,1-a]isoquinolin-6-yl)carbonyl]-1,1-dioxido-thiomorpholine.

31. A compound according to claim 1, which is: cis-1-{[3-(4-Fluorophenyl)-imidazo[5,1-a]isoquinolin-6-yl]carbonyl}-3,5-dimethyl-piperazine.

32. A compound according to claim 1, which is: cis-1-{[3-(2-Fluorophenyl)-imidazo[5,1-a]isoquinolin-6-yl]carbonyl}}-3,5-dimethyl-piperazine.

33. A compound according to claim 1, which is: cis-1-{[3-(Thien-3-yl)imidazo[5,1-a]isoquinolin-6-yl]carbonyl}-}}-3,5-dimethyl-piperazine.

34. A compound according to claim 1, which is: 1-{[3-(4-Chlorophenyl)-imidazo[5,1-a]isoquinolin-6-yl]carbonyl}pyrrolidine.

35. A compound according to claim 1, which is: 1-{[3-(Thien-3-yl)imidazo[5,1-a]isoquinolin-6-yl]carbonyl}-4-methyl piperidine.

36. A compound according to claim 1, which is: (R)-1-{[3-(Thien-3-yl)imidazo[5,1-a]isoquinolin-6-yl]carbonyl}-3-methyl-piperazine.

37. A compound according to claim 1, which is: (S-1-{[3-(Thien-3-yl)imidazo[5,1-a]isoquinolin-6-yl]carbonyl}-3-methyl-piperazine.

38. A compound according to claim 1, which is: 4-{[3-(Thien-3-yl)imidazo[5,1-a]isoquinolin-6-yl]carbonyl}morpholine.

39. A compound according to claim 1, which is: 1-{[3-(3-Fluorophenyl)-imidazo[5,1-a]isoquinolin-6-yl]carbonyl}pyrrolidine.

40. A compound according to claim 1, which is: cis-1-{[3-(Thien-3-yl)imidazo[5,1-a]isoquinolin-6-yl]carbonyl}-2,5-dimethylpiperazine.

41. A compound according to claim 1, which is: 1-{[3-(4-Methylisoxazol-3-yl)-imidazo[5,1-a]isoquinolin-6-yl]carbonyl}pyrrolidine.

42. A compound according to claim 1, which is: 4-{[3-(3-Fluorophenyl)-imidazo[5,1-a]isoquinolin-6-yl]carbonyl}morpholine.

43. A compound according to claim 1, which is: (R)-1-{[3-(3-Fluorophenyl)-imidazo[5,1-a]isoquinolin-6-yl]carbonyl}-2-hydroxymethyl-pyrrolidine.

44. A compound according to claim 1, which is: 1-{[3-(3-Fluorophenyl)-imidazo[5,1-a]isoquinolin-6-yl]carbonyl}piperidine.

45. A compound according to claim 1, which is: (S)-1-[(3-Phenylimidazo[5,1-a]isoquinolin-6-yl)carbonyl]-3-methylpiperazine.

46. A compound according to claim 1, which is: S)-1-{[3-(2-Fluorophenyl)-imidazo[5,1-a]isoquinolin-6-yl]carbonyl}-3-methylpiperazine.

47. A compound according to claim 1, which is: (S)-1-{[3-(4-Fluorophenyl)-imidazo[5,1-a]isoquinolin-6-yl]carbonyl}-3-methylpiperazine.

48. A compound according to claim 1, which is: S-1-{[3-(4-Methoxyphenyl)-imidazo[5,1-a]isoquinolin-6-yl]carbonyl}-homopiperazine.

49. A compound according to claim 1 of the formula

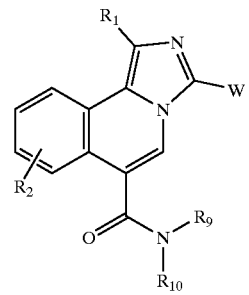

wherein
W is phenyl, isoxazolyl, thienyl, pyridyl, or quinolyl, each of which is optionally substituted with one, two, or three of $V_1$, $V_2$ and $V_3$, where $V_1$, $V_2$, and $V_3$ independently represent halogen, hydroxy, $C_1$–$C_6$ alkyl, $C_1$-$C_8$ alkoxy, —$NO_2$, —CN, amino, —NH($C_1$-$C_8$ alkyl), or —N($C_1$-$C_8$ alkyl)($C_1$-$C_8$ alkyl);

$R_2$ represents 0 to 2 groups independently chosen from hydrogen, halogen, hydroxy, $C_1$-$C_6$ alkyl, $C_1$-$C_8$ alkoxy, —$NO_2$, —CN, amino, —NH($C_1$-$C_8$ alkyl), and —N($C_1$-$C_8$ alkyl)($C_1$-$C_8$ alkyl);

$R_1$ is hydrogen, halogen, hydroxy, $C_1$-$C_6$ alkyl, $C_1$-$C_8$ alkoxy, —$NO_2$, —CN, amino, —NH($C_1$-$C_8$ alkyl), or —N($C_1$-$C_8$ alkyl)($C_1$-$C_8$ alkyl); and $R_9$ and $R_{10}$ are independently hydrogen or $C_1$-$C_8$ alkyl; or $R_9$ and $R_{10}$ together represent a $C_4$-$C_6$ straight chain alkylene group which together with the nitrogen atom to which $R_9$ and $R_{10}$ are attached form a 5- to 7-membered ring optionally containing one or two double bonds, O and/or N—$R_8$ where $R_8$ is hydrogen, $C_1$-$C_8$ alkyl, or HAr—($C_1$-$C_8$)alkyl, where HAr is phenyl, pyridinyl, or pyrimidinyl, each of which is optionally substituted with one or two halogen, hydroxy, hydroxy($C_1$-$C_6$)alkyl, $C_1$-$C_6$ alkyl, $C_1$-$C_8$ alkoxy, —$NO_2$, —CN, amino, —NH($C_1$-$C_8$ alkyl), or —N($C_1$-$C_8$ alkyl)($C_1$-$C_8$ alkyl).

50. A compound according to claim 1 of the formula

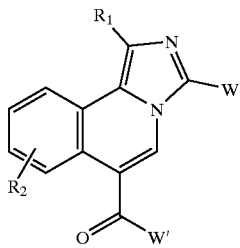

wherein

W is phenyl, isoxazolyl, thienyl, pyridyl, or quinolyl, each of which is optionally substituted with one, two, or three of $V_1$, $V_2$ and $V_3$, where $V_1$, $V_2$, and $V_3$ independently represent halogen, hydroxy, $C_1$-$C_6$ alkyl, $C_1$-$C_8$ alkoxy, —$NO_2$, —CN, amino, —NH($C_1$-$C_8$ alkyl), or —N($C_1$-$C_8$ alkyl)($C_1$-$C_8$ alkyl);

$R_2$ represents up to 2 groups independently chosen from hydrogen, halogen, hydroxy, $C_1$-$C_6$ alkyl, $C_1$-$C_8$ alkoxy, —$NO_2$, —CN, amino, —NH($C_1$-$C_8$ alkyl), or —N($C_1$-$C_8$ alkyl)($C_1$-$C_8$ alkyl);

$R_1$ is hydrogen, halogen, hydroxy, $C_1$-$C_6$ alkyl, $C_1$-$C_8$ alkoxy, —$NO_2$, —CN, amino, —NH($C_1$-$C_8$ alkyl), or —N($C_1$-$C_8$ alkyl)($C_1$-$C_8$ alkyl; and W' represents
(i) phenyl optionally substituted with one, two, or three of $T_1$, $T_2$ and $T_3$, where $T_1$, $T_2$, and $T_3$ independently represent halogen, hydroxy, $C_1$-$C_6$ alkyl, $C_1$-$C_8$ alkoxy, —$NO_2$, —CN, amino, —NH($C_1$-$C_8$ alkyl), or —N($C_1$-$C_8$ alkyl)($C_1$-$C_8$ alkyl);
(ii) —OR where R is $C_1$-$C_8$ alkyl or aryl($C_1$-$C_6$)alkyl; or
(iii) $M_5$ where $M_5$ is hydroxy, $C_1$-$C_8$ alkyl, aryl($C_1$-$C_6$) alkyl or —N($C_1$-$C_4$ alkyl)($C_1$-$C_4$ alkoxy).

51. A pharmaceutical composition comprising a compound according to claim 1 combined with at least one pharmaceutically acceptable carrier or excipient.

52. A method for the treatment of anxiety, depression, a sleep disorder, or cognitive impairment said method comprising administering to a patient in need of such treatment an effective amount of a compound of claim 1.

53. A method for localizing $GABA_A$ receptors in a tissue sample comprising:

contacting with the sample a detectably-labeled compound of claim 1 under conditions that permit binding of the compound to $GABA_A$ receptors, washing the sample to remove unbound compound, and detecting the bound compound.

54. A method of inhibiting the binding of a benzodiazepine compound to a $GABA_A$ receptor, said method comprising contacting a compound of claim 1 with cells expressing the $GABA_A$ receptor, in the presence of the benzodiazepine, wherein the compound is present at a concentration sufficient to inhibit the binding of the benzodiazepine compound to the $GABA_A$ receptor in vitro.

55. A method for altering the signal-transducing activity of $GABA_A$ receptors, said method comprising exposing cells expressing the $GABA_A$ receptors to a compound according to claim 1 at a concentration sufficient to inhibit RO15-1788 binding to cells expressing a cloned human $GABA_A$ receptor in vitro.

56. A packaged pharmaceutical composition comprising the pharmaceutical composition of claim 51 in a container and instructions for using the composition to treat a patient suffering from anxiety, depression, a sleep disorder, attention deficit disorder, Alzheimer's dementia, or cognitive impairment.

57. A compound according to claim 1 wherein in a assay of $GABA_A$ receptor binding that determines the displacement of $^3$H-Flumazenil from rat cortical tissue in 0.05 M Tris HCl buffer at 4° C. the compound exhibits an $K_i$ of 1 micromolar or less.

58. A compound according to claim 1 wherein in a assay of $GABA_A$ receptor binding that determines the displacement of $^3$H-Flumazenil from rat cortical tissue in 0.05 M Tris HCl buffer at 4° C. the compound exhibits an $K_i$ of 100 nanomolar or less.

59. A compound according to claim 1 wherein in a assay of $GABA_A$ receptor binding that determines the displacement of $^3$H-Flumazenil from rat cortical tissue in 0.05 M Tris HCl buffer at 4° C. the compound exhibits an $K_i$ of 10 nanomolar or less.

* * * * *